(12) United States Patent
Fujimura et al.

(10) Patent No.: US 11,471,141 B2
(45) Date of Patent: Oct. 18, 2022

(54) POWDER SPRAY DEVICE AND MEDICAL ADHESIVE EXCELLENT IN SELF-DECOMPOSABILITY AND ADHESIVENESS

(71) Applicant: BMG Incorporated, Kyoto (JP)

(72) Inventors: Motoki Fujimura, Kyoto (JP); Shinichi Osada, Kyoto (JP); Yusuke Kojitani, Kyoto (JP); Woogi Hyon, Kyoto (JP); Suong-Hyu Hyon, Kyoto (JP)

(73) Assignee: BMG INCORPORATED, Kyoto (JP)

( * ) Notice: Subject to any disclaimer, the term of this patent is extended or adjusted under 35 U.S.C. 154(b) by 113 days.

(21) Appl. No.: 16/894,294

(22) Filed: Jun. 5, 2020

(65) Prior Publication Data

US 2021/0378649 A1 Dec. 9, 2021

(51) Int. Cl.
*A61B 17/00* (2006.01)
*A61L 24/04* (2006.01)

(52) U.S. Cl.
CPC ...... *A61B 17/00491* (2013.01); *A61L 24/043* (2013.01); *A61B 2017/00522* (2013.01)

(58) Field of Classification Search
CPC .... A61B 2017/00522; A61B 17/00491; A61B 2017/00495; A61B 2017/005; A61B 2017/00504; A61B 2017/00508; A61B 2017/00513; A61B 2017/00517; A61L 24/043; A61M 2202/064; A61M 11/00; A61M 11/001; A61M 11/002;
(Continued)

(56) References Cited

U.S. PATENT DOCUMENTS

| 4,184,258 | A | * | 1/1980 | Barrington | ............. | A61C 3/025 |
| | | | | | | 222/636 |
| 4,446,316 | A | * | 5/1984 | Chazov | .......... | C12Y 304/21007 |
| | | | | | | 536/112 |

(Continued)

FOREIGN PATENT DOCUMENTS

| EP | 1438079 B1 | 4/2005 | |
| EP | 2100628 A1 * | 9/2009 | ........... A61L 31/148 |

(Continued)

*Primary Examiner* — Kathleen S Holwerda
*Assistant Examiner* — Kankindi Rwego
(74) *Attorney, Agent, or Firm* — United IP Counselors, LLC

(57) ABSTRACT

A powder spray device includes a funnel member, a first three-way joint, an air-current supply tube, a discharge tube, a vibration motor, a bypass air-current tube, and a switching mechanism. The first three-way joint has a first opening connected to an outlet at a lower end of the funnel member. The air-current supply tube and discharge tube are respectively connected to second and third openings of the first three-way joint. The vibration motor is fixed onto an outer surface of a funnel body of the funnel member. The bypass air-current tube branches off from the air-current supply tube and is connected to the discharge tube. The switching mechanism switches from and to standby state, in which compressed gas is sent only through the bypass air-current tube, to and from spray-coating state, in which compressed gas is sent out through the air-current supply tube, and also through the bypass air-current tube.

15 Claims, 8 Drawing Sheets

(58) Field of Classification Search
CPC .. A61M 11/003; A61M 11/005; A61M 11/02; B05B 7/14; B05B 7/1422; B05B 7/1445; B05B 7/1459; B05B 7/1463; B05B 7/1468; B05B 7/1472; B05B 7/1477; B05B 7/1481; B05B 7/1486; B05B 1/16; B05B 1/1609; B05B 1/1618; B05B 1/1627; B05B 1/1636; B05B 1/1645; B05B 1/1654; B05B 1/1663; B05B 1/1672; B05B 1/1681; B65D 83/14; B65D 83/384
USPC .................................. 606/214; 604/58, 140
See application file for complete search history.

(56) References Cited

U.S. PATENT DOCUMENTS

| | | | | |
|---|---|---|---|---|
| 6,776,361 | B1* | 8/2004 | Watanabe | B30B 15/0011 239/654 |
| 2003/0077384 | A1* | 4/2003 | Krysa | B05B 7/1486 427/180 |
| 2005/0002893 | A1 | 1/2005 | Goldmann | |
| 2008/0319101 | A1* | 12/2008 | Nakajima | A61L 24/043 523/111 |
| 2011/0251580 | A1* | 10/2011 | Greenhalgh | A61M 11/008 604/500 |
| 2013/0046278 | A1* | 2/2013 | Ji | A61M 11/008 604/500 |
| 2013/0218072 | A1* | 8/2013 | Kubo | A61M 15/0006 604/58 |
| 2017/0296760 | A1* | 10/2017 | Lee | A61B 17/0057 |

FOREIGN PATENT DOCUMENTS

| | | |
|---|---|---|
| JP | 2016-063919 A | 4/2016 |
| WO | 2003/035122 A1 | 5/2003 |
| WO | 2006/080523 A1 | 8/2006 |
| WO | 2008/066182 A1 | 6/2008 |

* cited by examiner

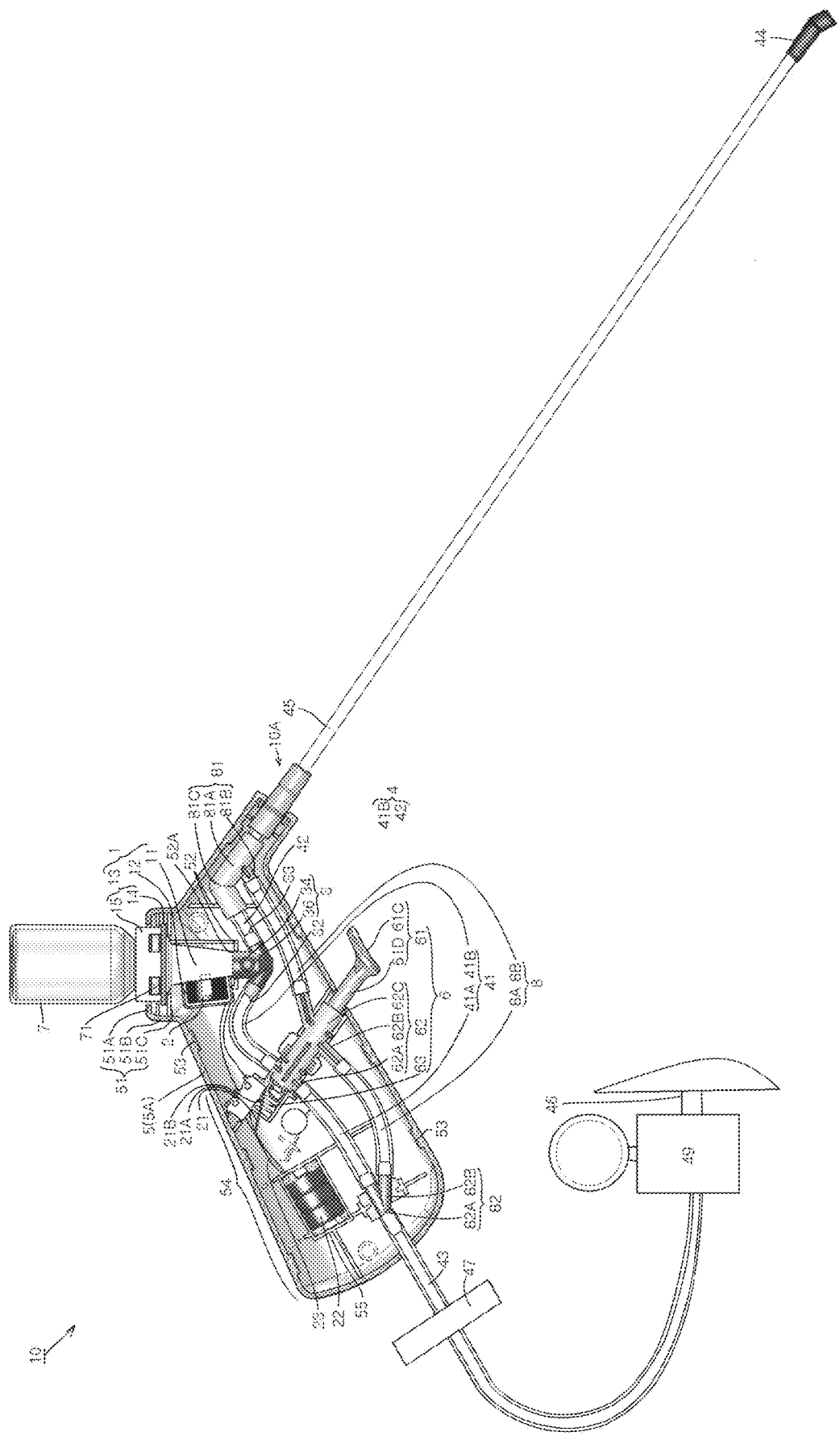
[Fig1]

[Fig2]
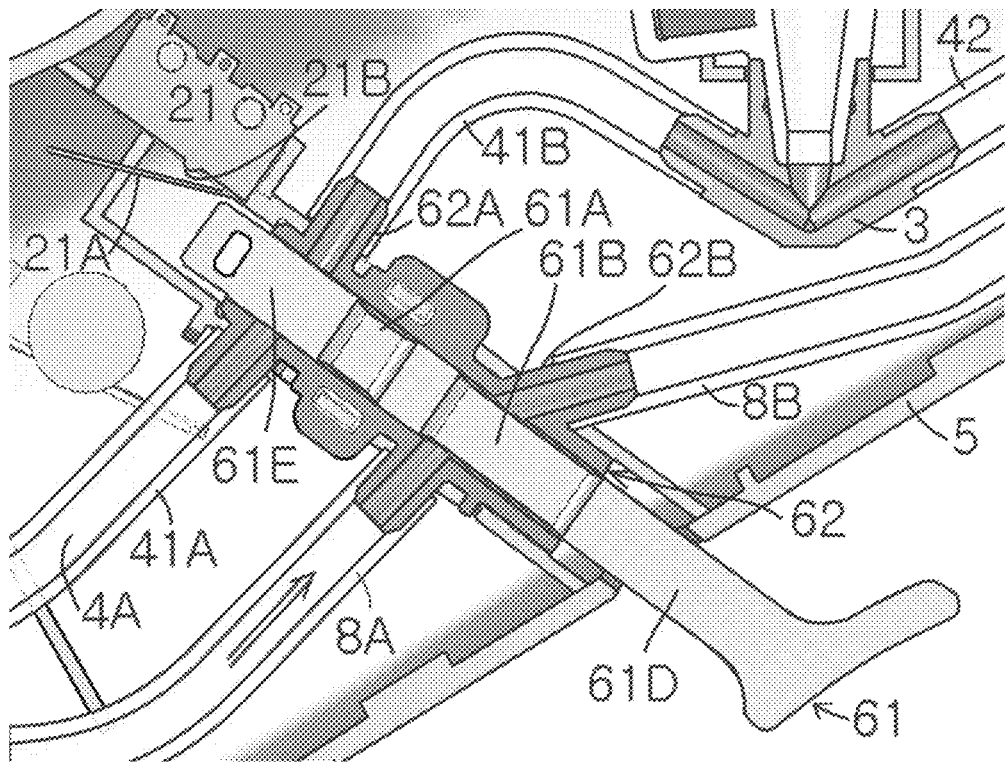
[Fig3]
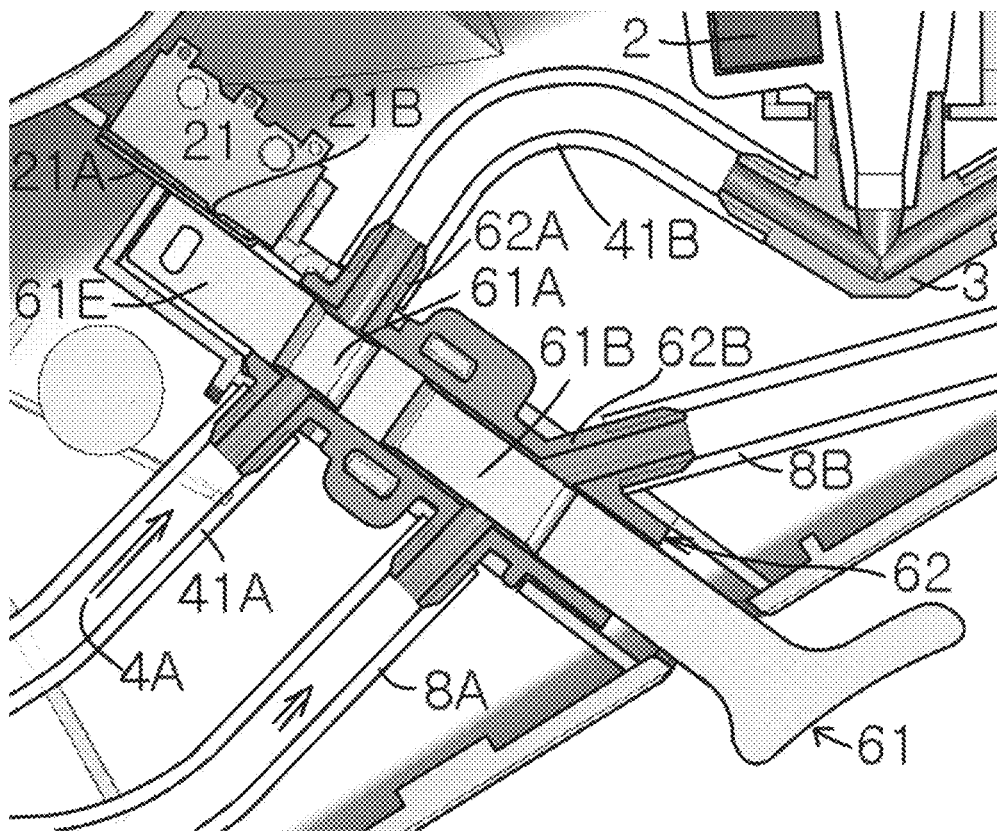

[Fig4]
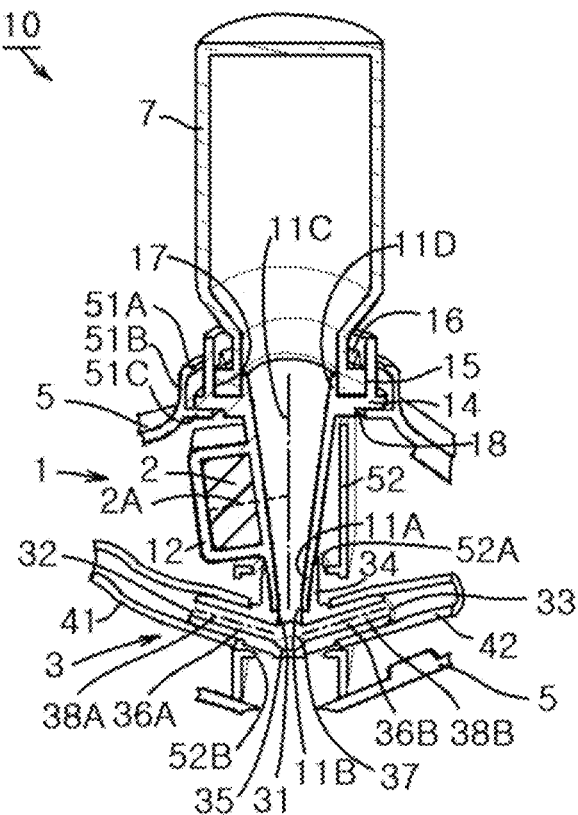
[Fig5]
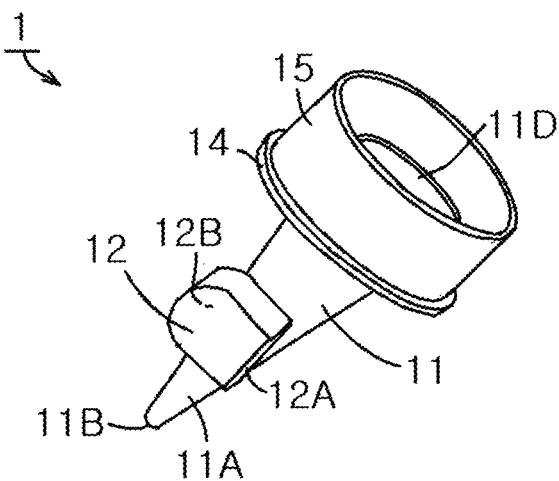

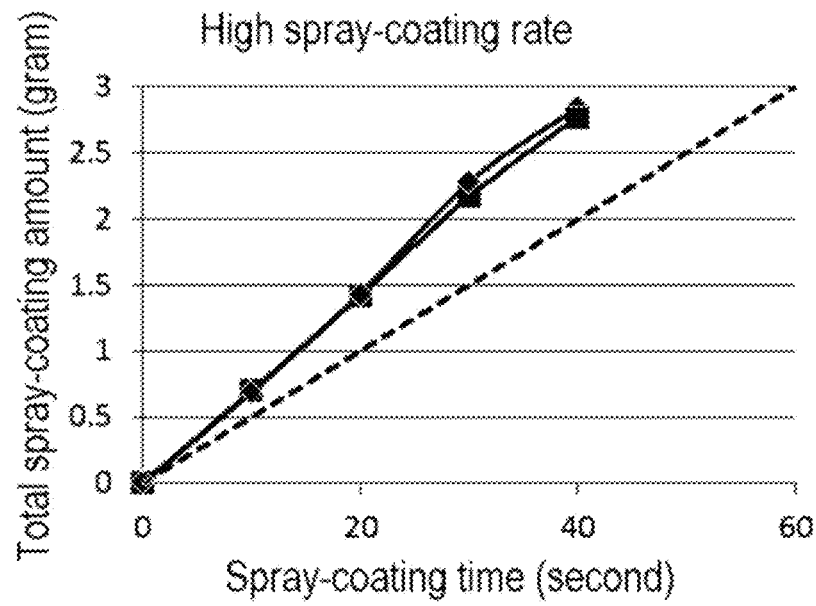
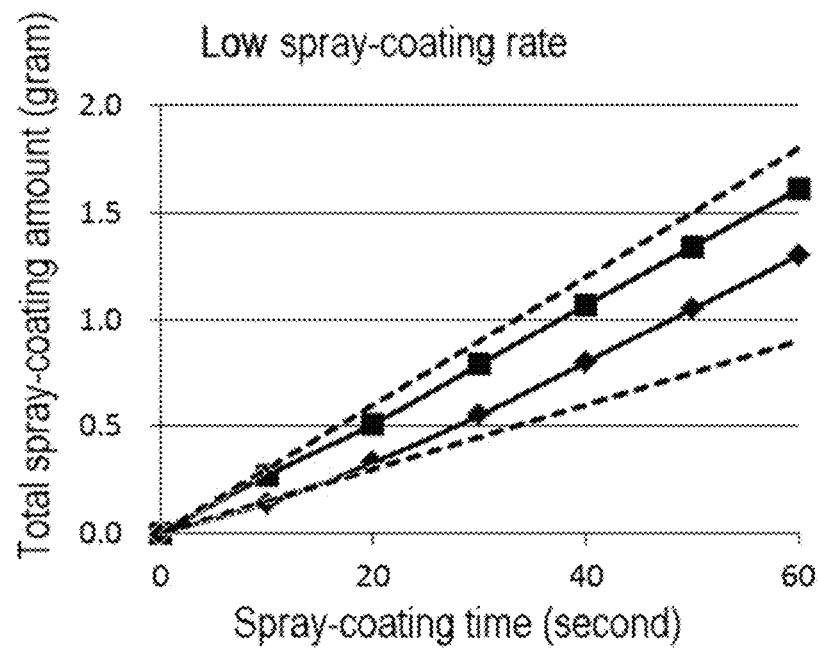

[Fig8]

| Spray-coating amount per unit area (mg/cm²) | Image of spray-coated surface | Image of two-minutes after gelation | Powder remained | Burst pressure* (mmHg) |
|---|---|---|---|---|
| 11 | | | No | 68.5 |
| 25 | | | No | 141.1 |
| 45 | | | No | 173.8 |
| 77 | | | Yes | 53.4 |

*Burst pressure: Maximum leak-free pressure for preventing air leak at pin-hole occlusion test when being sealed with varied spray-coating amount per unit area

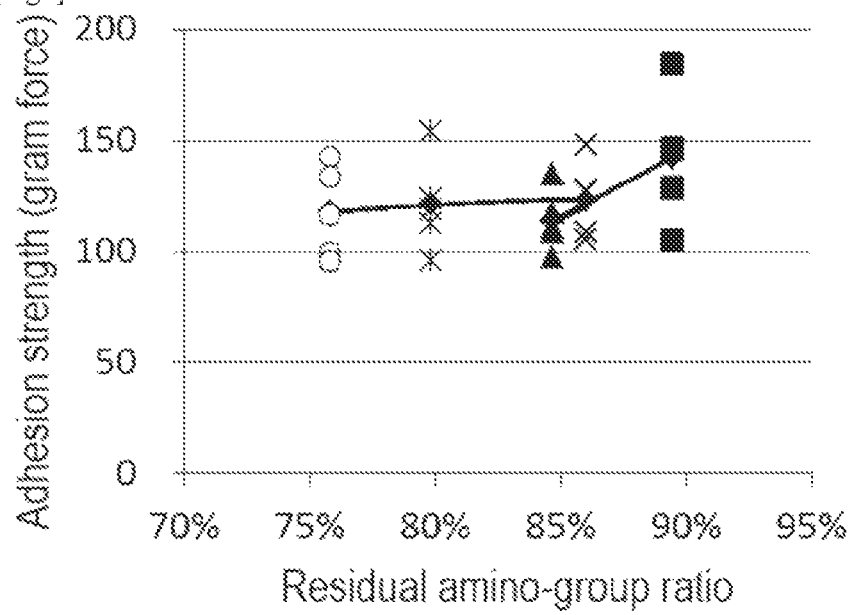
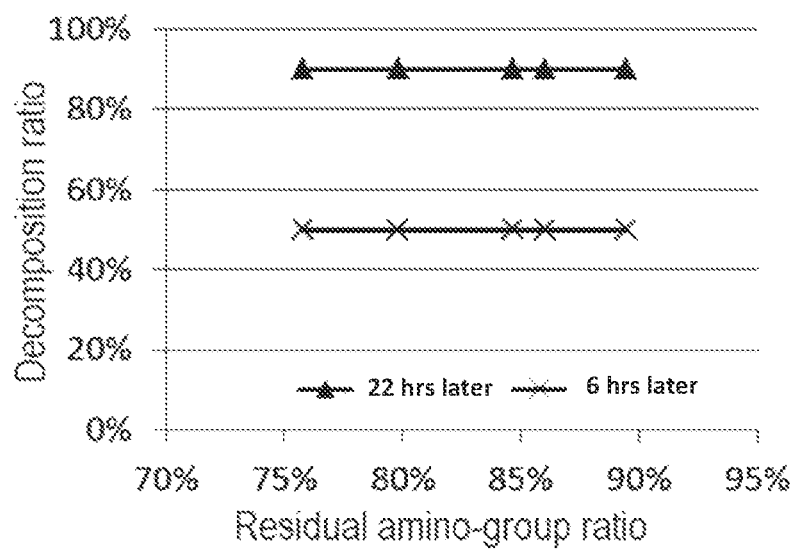

[Fig11]
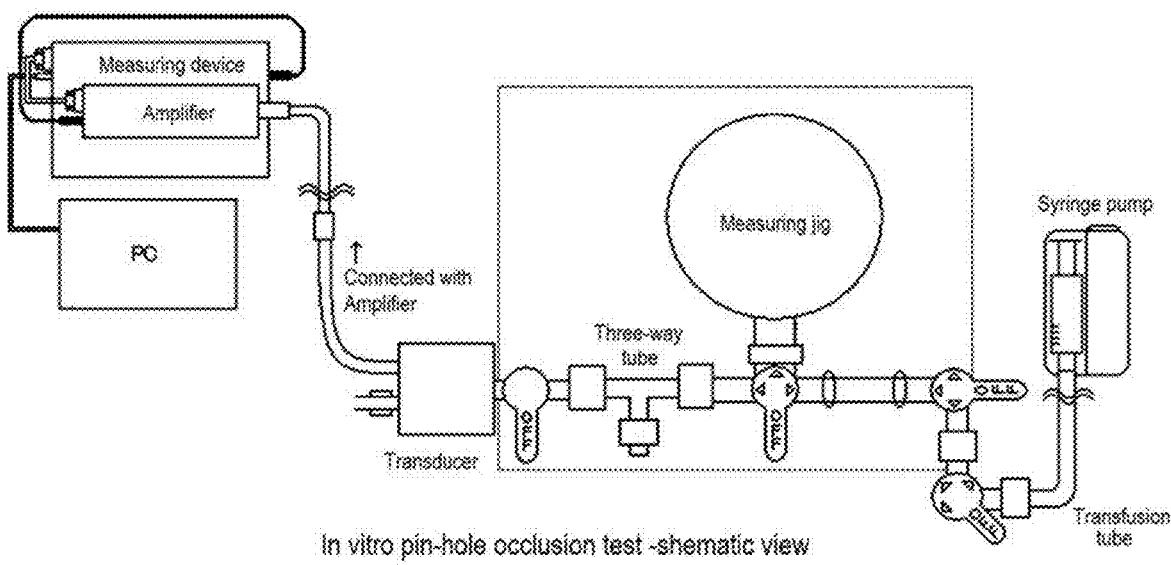
In vitro pin-hole occlusion test -shematic view
[Fig12]
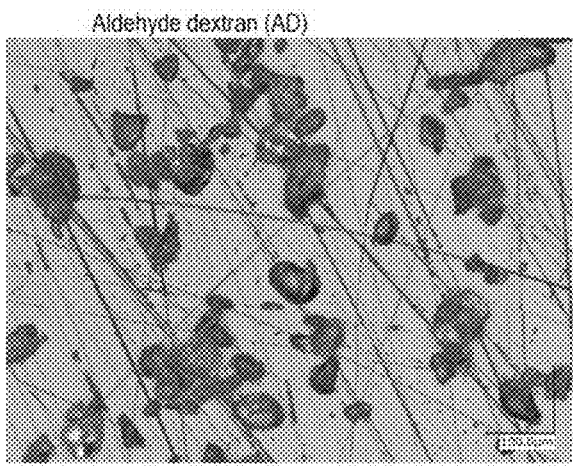
[Fig13]
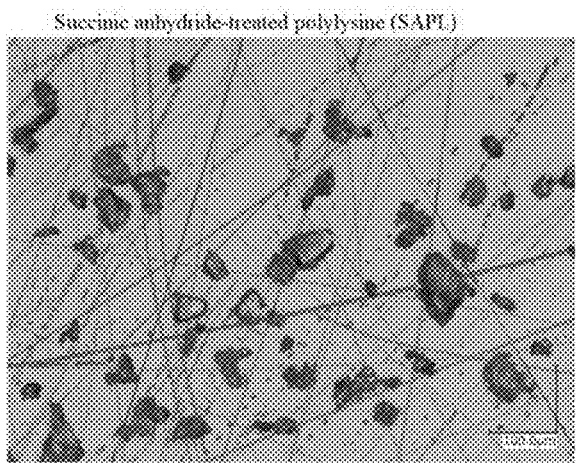

[Fig14]
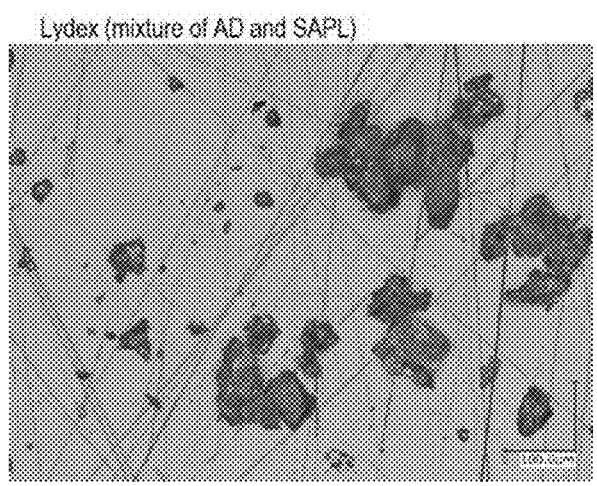

POWDER SPRAY DEVICE AND MEDICAL ADHESIVE EXCELLENT IN SELF-DECOMPOSABILITY AND ADHESIVENESS

CROSS-REFERENCE TO RELATED APPLICATIONS

The entire disclosure of Japanese Patent Application No. 2017-222915, filed on Nov. 20, 2017, which was published as Japanese Patent Application Publication No. 2019-092645 on Jun. 20, 2019 is hereby incorporated by reference.

TECHNICAL FIELD

The present invention relates to a powder spray device, especially for a medical adhesive used for preventing leakage, obstruction, adhesion, filling, and adhesion of living tissue at the time of a surgical operation or the like, and hemostasis, as well as such medical adhesive. In particular, the medical adhesive is comprised of a powder containing the first reaction component (powder reactant) and a powder containing the second reaction component (powder reactant), and the first and second reaction component are reacted with each other in the presence of water. The medical adhesive is decomposed, fluidized and excreted after a certain period of time after the reaction components are allowed to react with each other and hardened into a gel.

BACKGROUND ART

As adhesives for medical use, particularly for surgical operations, (1) cyanoacrylate adhesives and (2) fibrin glue have been mainly used. However, the cyanoacrylate-based adhesive has a problem that the solidified material has poor flexibility and is hard and may hinder wound healing, and is difficult to be decomposed in a living body, so that it is easily encapsulated and becomes a foreign substance. On the other hand, since the fibrin glue has a considerably low adhesive strength, the generated fibrin clots may come off from the tissue. Furthermore, there is a problem that virus infection is a concern because the fibrin glue is a blood product.

Recently, investigated are (3) aldehyde dextran-polymer chitosan (WO2003/035122, AESCULAP AG & CO KG (DE), a counter part of US2005/0002893 A-1 and EP1438079 B), (4) micelle-forming terminal aldehyde polymer-polymer polyallylamine, (5) aldehyde-modified starch-collagen, (6) gelatin-succinimidated poly-L-glutamic acid, (7) gelatin-dicarboxylic anhydride, and (8) Urethane prepolymers and so on, but each of these has a problems (see the Background Art section of WO/2006/080523).

Therefore, the research group of the present applicant has conducted various searches and studies, and attempted use in place of the above-mentioned polymer chitosan, a partially carboxylated poly-L-lysine, which is obtained by modifying ε-poly-L-lysine having a relatively low molecular weight, by partially blocking its side-chain amino groups with a carboxylic anhydride such as succinic anhydride. As a result, it has been developed, while sufficiently satisfying the general properties required for medical adhesives, while rapidly disintegrating after the elapse of the designed disintegration time, a medical adhesive capable of relatively freely adjusting and controlling the design disintegration time as well as a hydrogel resin for medical use (WO/2006/080523 and WO/2008/066182).

On the other hand, as a result of various studies, this research group has developed a powder-spray device (JP2016-63919A), by which various powders, such as powders with low bulk density and low fluidity, can be continuously and as uniformly discharged as possible by compressed air or pressurized gas. This powder spray device is used particularly for a practitioner, such as a surgeon, to accurately apply a medical adhesive, which has been developed by the present research group, to a diseased part or the like in a predetermined area and in a predetermined amount.

The medical two-component reactive adhesive developed earlier by this research group has excellent performance and characteristics that satisfy all of: (1) high adhesiveness to a living-tissue adherent containing water, and (2) comparatively rapid hardening reactivity on the surface of a living tissue under room temperature and atmospheric pressure; and (3) flexibility until the wound is healed while remaining in close contact with the adherent, such as skin, blood vessels, or organs, without impairing the physical movement of the adherent.

The present inventors have worked diligently to ensure that stable performance is obtained by using the two-component reactive adhesive when actually used for medical use. The inventors have found that particularly excellent adhesiveness and its reliability are achievable, as compared to the level specifically tested previously, when the partial amino acid content of the partially carboxylated-poly-L-lysine is set to a higher specific range, and the above powder spraying apparatus was used by setting the applied amount to a lower specific range.

BRIEF SUMMARY

The two-component reactive adhesive for medical use of the present invention comprises: a first reactant comprising a powder of aldehyde-modified glucan having a weight average molecular weight of 1,000 to 200,000; and a second reactant comprising a powder of partially carboxylated poly-L-lysine, which has been obtained by reacting poly-L-lysine having a weight average molecular weight of 1,000 to 20,000 with succinic anhydride or glutaric anhydride so that the residual amino group ratio becomes 70 to 93%; and the first and second reactants are mixed with each other so that aldehyde-to-amino group ratio becomes in a range of 0.9 to 2.0. The aldehyde-modified glucan is obtained by oxidizing dextran or dextrin with periodate so that 0.2 to 0.5 aldehyde groups is introduced per anhydroglucose unit. The mixed powder has a water content of 2.0% or less, and the amount of one-time application operation using the powder spray device is 20-50 mg/cm$^2$.

Preferably, the residual amino group ratio in the partially carboxylated poly-L-lysine is 87 to 93%. In this way, a particularly high adhesive strength and its reliability are obtained.

In the two-component reactive adhesive for medical use of the present invention, the hydrogel is disintegrated in varied periods of time, by changing the amount of aldehyde groups introduced in the aldehyde-modified glucan in the range of 0.2 to 0.4 per anhydroglucose unit. By such changing, the period of time required to be disintegrated can be adjusted and set in a range from two to three days to four weeks or more.

The powder spraying apparatus used in the preferred embodiment of the medical two-component reactive adhesive has: a funnel member capable of mounting a powder container on the top or integrally provided with the powder container; a three-way joint, first opening of which is connected to the discharge port at the lower end of the funnel member; an air flow supply tube, which is connected to second opening of the three-way joint; a discharge tube, which is connected to third opening of the three-way joint; and a housing for accommodating these members. The powder spraying apparatus further comprises a vibration motor, wherein the funnel member is provided integrally with a pocket portion on the outer surface of the funnel body portion, into which the vibration motor is pushed in and fixed, and wherein the funnel member and the three-way joint are attached to the housing so as to be able to be shaken and swung while clearances are kept between these members.

The powder spray device according to the present invention, in the powder spray device as described above, comprises a switching (On/Off) mechanism (6) for switching between: a standby state (Off state) in which the compressed gas is sent only through the bypass air-current tube (8); and spray coating state (On state), in which the compressed gas is sent through a spray-coating air-current tube line comprising the air-current supply tube (41), the inside of the three-way joint (3), and the discharge tube (42) and also through the bypass air-current tube (8).

The funnel member and the three-way joint are held in the housing by a large clearance (play) so as to be able to swing back and forth, right and left, and up and down. Further, they are held in a manner as swingable as centered on the pocket portion for example. That is, the funnel member and the three-way joint are held in the housing with sufficient clearance (play) so as to be able to swing in every direction and to swing to vary the axial direction. In addition, the mounting structure restricts the movable range so as not to come off. In a preferred embodiment, a movable dimension range for vertical swinging as a result of the clearance is 0.5 to 8 mm, preferably 1 to 5 mm, and particularly 2 to 4 mm. A movable dimension range for horizontal swinging as vertical to the center axis of the funnel body is 0.5 to 5 mm, preferably 0.5 to 4 mm, in particular 2 to 3 mm. In a preferred embodiment, the funnel member is held from the housing in vicinities of upper and lower ends of the funnel body. The largest swing movement occurs when the vicinity of the upper end and the vicinity of the lower end of the funnel body move in opposite directions to each other up to the limit of the horizontal swingable range. In a preferred embodiment, the swingable retaining and movable range restriction from the housing to the funnel member in vicinity of the upper end of the funnel body are realized by butting between the flanges and between the flange and the cylindrical portion at top of the housing. Specifically, the movable range can be limited such that a flange, which is provided on one of the funnel member and the housing, abuts against upper and lower flanges and the cylindrical portion provided, which are provided on the other of the funnel member and the housing. Also, in a preferred embodiment, the swingable retaining and movable range restriction between the housing, the funnel member and the three-way joint in vicinity of the lower end of the funnel body are realized by butting of the walls or ribs of the housing onto the three-way joint or the lower end of the funnel body. Specifically, they are realized by that: the lower end of the funnel body or a part of the three-way joint is movably inserted in a circular or otherwise shaped opening provided in the bottom wall of the housing or in the horizontal plate-shaped rib of the housing. In the preferred embodiment, the flange protrudes radially outward or inward in a plate shape to form an edge at the tip. However, the flange may have a cross-sectional shape other than a plate shape, or may be a stepped portion or a bent portion having a U-shaped cross section, which is provided on a part of the cylindrical wall. For example, a radial protrusion having near square shaped rectangular or lateral U-shaped cross section may be retained, with a large clearance, in a recess provided in a part of the cylindrical wall.

A vibration motor typically has a ballast (weight), such as a fan-shaped metal piece, mounted on a central shaft so as to be deflected to one side, and generates vibration by the rotation of the ballast. The vibration motor is preferably of the flat type. That is, the diameter is larger than the dimension in the rotation axis direction. The vibration motor is more preferably of the coin type. That is, it has a disk shape with a diameter of 25 mm or less, for example, a diameter of 5 to 20 mm. The thickness is, for example, 20 to 60% of the diameter. The rotation speed (rotations per minute) of the vibration motor is, for example, 1000 to 20,000 rpm (frequency of about 20 to 300 Hz), particularly 2000 to 10,000 rpm (frequency of about 30 to 200 Hz). The pocket for accommodating the vibration motor has dimensions respectively equal to or slightly smaller than those of the vibration motor so that the vibration motor is pushed in and fixed in the pocket. The pocket is preferably arranged such that the axis of rotation of the drive motor is directed towards the inside of the funnel body, in particular the extension of the axis of rotation intersects or substantially intersects the central axis of the funnel body. In a preferred embodiment, the opening of the pocket is oriented in the circumferential direction of the funnel body, and preferably, in order to prevent the vibration motor from slipping out and/or to further secure the vibration motor, the opening or the inner surface of the pocket is provided with a latching protrusion, an attached adhesive tape or a layer of a pressure-sensitive adhesive. The latching protrusion may be provided, for example, as an arc-shaped ridge protruding from the inner surface of the pocket, or as a claw at a fringe of the opening. The adhesive tape may be, for example, of a single-sided adhesive type attached to cover up the opening, and may be a double-sided adhesive type sandwiched between the inner surface of the pocket and the vibration motor. The adhesive may be applied, for example, to the inner surface of the pocket before pushing the vibration motor into the pocket. The pressure-sensitive adhesive to be applied or used for the pressure-sensitive adhesive tape is, for example, a modified acrylic resin or a modified silicone resin. When the pressure-sensitive adhesive is used for a pressure-sensitive adhesive tape, the adhesive would pass, for example, requirements of first grade of JIS Z 1541. If a strong pressure-sensitive adhesive or pressure-sensitive adhesive tape is used, it is possible to simply and reliably prevent the vibration motor from coming off.

In a preferred embodiment, at least the funnel body and the pocket are integrally provided in the funnel member by resin molding. The resin molding can be performed by injection molding, extrusion molding, or the like, and preferably, a polyolefin resin including a polyethylene resin, a polypropylene resin, a polymethylpentene resin, and a copolymer resin thereof is used.

The medical two-component reactive adhesive used in the preferred embodiment may be stored in advance as a mixture of the powder of the first reactant and the powder of the second reactant in a bottle, and such powder mixture may be applied by the above powder spray device or the like.

Generally, for medical purposes, medical adhesives must ensure storage stability for at least one year. It is desirable that the storage stability is ensured for at least 12 months, preferably at least 18 months, more preferably at least 24 months, even more preferably at least 30 months.

The aldehyde-modified glucan constituting the first reactant is obtained by oxidizing α-glucan to introduce an aldehyde group, and has a weight average molecular weight in the range of 1,000 to 200,000. Alpha-glucan is a sugar chain in which glucoses are dehydrated and condensed to form an a bond, and the molecular weight of a sugar residue (anhydroglucose unit) in glucan is 162.14. The α-glucan used in the present invention includes dextran, dextrin, and pullulan, and these can be used as a mixture. Starch and amylose can be used if they are appropriately decomposed. High molecular pullulan products can also be used after being appropriately decomposed. In some cases, a glucan comprising α-glucan units and β-glucan units can be used in the same manner as α-glucan as long as it can be dissolved or uniformly dispersed in water. The introduction of the aldehyde group can be carried out by a typical periodate oxidation method, and is preferably by an amount of 0.1 to 1.0 aldehyde groups per anhydroglucose unit, more preferably by an amount of 0.2 to 0.9, even more preferably by an amount of 0.2 to 0.6 aldehyde groups per anhydroglucose unit, in order to impart appropriate self-decomposability. In order to enhance the storage stability of the first reactant, the degree of aldehyde conversion should be relatively low so that, for example, 0.2 to 0.4 aldehyde groups per anhydroglucose unit are introduced. By using the adhesive powder mixture, curing can be realized in a sufficiently short time even if the introduction amount of the aldehyde group is 0.2 to 0.4 per anhydroglucose unit.

Among aldehyde-modified α-glucans, aldehyde-modified dextran and aldehyde-modified dextrin are particularly preferred for reasons such as stability of adhesive performance. The dextran used to obtain the aldehyde dextran has a weight average molecular weight of preferably 2,000 to 200,000, more preferably 2,000 to 100,000. The weight average molecular weight of dextrin is, for example, 1,000 to 10,000. The optimum molecular weight of the aldehyde-modified α-glucan varies depending on the specific application, and the period until liquefaction by self-decomposition can be adjusted by selecting a specific molecular weight or a molecular weight distribution. If the molecular weight of the aldehyde-modified α-glucan is too large, liquefaction due to autolysis or self-decomposition will be excessively delayed. If the molecular weight of the aldehyde-modified α-glucan would be too small, the time for maintaining the gelled state would be too short.

As the powder of the aldehyde-modified glucan (first reactant), a powder obtained, after introducing an aldehyde group by periodate oxidation, by drying and then mechanically pulverizing the aldehyde-modified glucan product may be used as it is. In some cases, the powder can be formed by spray drying at a relatively low temperature, under reduced pressure or while blowing an inert gas such as nitrogen.

The partially carboxylated poly-L-lysine constituting the second reactant comprises a chain of L-lysine and has a weight average molecular weight of 1,000 to 20,000, preferably 1,000 to 10,000, more preferably 1500 to 8,000. In addition, preferably, the poly-L-lysine does not substantially contain a high molecular weight fraction having a molecular weight of 30,000 or more. Particularly, the poly-L-lysine is preferably ε-poly-L-lysine having a molecular weight of 1,000 to 20,000, particularly 1,000 to 6,000, which is produced by using a microorganism or an enzyme.

An acid or an acid salt as a pH adjuster is added to the second reactant or the first reactant, if necessary. Preferably, a monovalent or polyvalent carboxylic acid or its anhydride is added. In this way, when the first reactant and the second reactant are mixed, the pH is in the range of 5.0 to 8.0, preferably in the range of 5.5 to 7.5, more preferably in the range of 6.5 to 7.5.

The ε-poly-L-lysine as the amino group-containing polymer used as the second reactant may be obtained from a 10% by weight "neutral polylysine aqueous solution", through drying and mechanical pulverization in the same manner as in the case of the above-mentioned aldehyde dextran. The resulting product can be used as is as succinic anhydride-treated polylysine or as a second reactant. In a preferred embodiment, the "neutral polylysine aqueous solution" is prepared by adding 0.5 g of succinic anhydride and 14.5 ml of distilled water to 10 ml of a 25 wt % ε-polylysine aqueous solution (molecular weight: 4,000, JNC (Chisso) Corporation, free amine).

Any form is adoptable for the powder of aldehyde-modified glucan as the first reactant and the powder of partially carboxylated poly-L-lysine as the second reactant, as long as they have excellent dispersibility and solubility. The form of the powder is preferably a porous body having a random shape. For this reason, a powder obtained by drying an aqueous solution and then pulverizing mechanically is preferable. When such a powder is obtained, it is not only excellent in sprayability but also preferable for blocking leaks, particularly for blocking air leaks. It is considered that the resin takes a moderately heterogeneous solution structure during the reaction of curing and performs a moderately heterogeneous reaction in a micro order, resulting in a tougher cured resin. The average particle size of the powder gradually becomes more preferable as it progresses from the following range (1) to (4): (1) 10 to 150 μm; (2) 15 to 120 μm; (3) 20 to 100 μm; and (4) 20 to 80 μm. That is, the average particle size is most preferably 20 to 80 μm. Here, the average particle diameter is determined by using an image analysis program (for example, an image analysis type particle size distribution measurement software "Mac-View" of Mountech Co., Ltd.) from an image obtained by a stereoscopic microscope. It is obtained by calculating the two-axis average diameter (simple average x of the major axis length and the minor axis length of the particle) and then taking the average diameter ($\Sigma x^2/\Sigma x$). The aspect ratio (major axis length/minor axis length) of the powder is, for example, in a range of 1.3 to 3.0, particularly 1.5 to 2.0.

Mixing the powders of the first reactant and the second reactant so as to form an adhesive powder mixture having a predetermined reaction molar ratio not only facilitates spraying but also improves the leak pressure, especially improves the obstruction of air leakage. When such adhesive powder mixture is used, even if it is stored in a bottle or a syringe and vibrated, the mixing ratio of the powders of the first and second reactants does not locally fluctuate due to the classifying action. When the adhesive powder mixture is stored in a vial bottle or the like after being plugged, the water content is kept at 5.0% or less, preferably 2.0% or less, still more preferably around 1.0%, for example, in a range of 0.5% to 1.5%. The same applies to the case where the powder of only the first reactant is stored.

The molar ratio of aldehyde groups to amino groups in the state where the first reactant and the second reactant are mixed is preferably in a range of 0.9 to 2.5, more preferably in a range of 0.9 to 2.0. Such range is preferable to keep the adhesive strength high. Further, adopting such range enables to decrease the remaining aldehyde group or amino group and thus is meaningful in further reducing toxicity.

The first reactant and the second reactant can be easily sterilized by radiation sterilization using gamma rays, electron beams or the like in the state of an adhesive powder mixture. Preferably, sterilization is performed by irradiating with radioactive ray of 10 to 50 kGy, more preferably of 20 to 30 kGy in a sealed state in a vial bottle or the like. A closed container such as a vial bottle can be filled with the adhesive powder mixture so that, for example, even after sterilization, 60% or more, particularly 80% or more of the volume of the closed container is filled. Further, the water content of the mixed adhesive powder at this time can be, for example, 0.5 to 2.0%, particularly 0.5 to 1.0%. When the sterilizing operation is performed under such conditions, the fluidity of the mixed adhesive powder can be improved to the extent necessary for application by the powder spray device. This is a completely unexpected effect. This is presumed to be due to the fact that the moisture contained in the mixed adhesive powder is heated during radiation sterilization, so that the protrusions on surfaces of the powder are slightly rounded.

The first reactant and the second reactant can be sprayed together with compressed air by the above powder spray device in the state of the mixed adhesive powder, and applied by spraying. It is preferable to repeat the application operation by spraying or the like, that is, to perform the application operation two or more times, for example, two to four times, in order to achieve uniformity of application and the like. Moreover, by adjusting intensity of vibration in the powder spray device, it is able to spray quantitatively at any spray-coating rate, so that a uniform and thin layer is realized in a predetermined time. During and after such repetitive spray-coating operation, physiological saline or distilled water is added to the spray-coated area, by spraying, dripping, or the like. For example, the adding of saline or water may be performed by spraying, sprinkling or dripping with a small syringe, onto a tip of which a spraying adapter or a very small injection needle is attached, or by spraying or the like with a finger press type spray bottle for skin lotion. In addition, when no sufficient moisture or water exists in areas to be bonded or the lesion area, physiological saline or the like may be dropped or sprayed on beforehand of the first application of the mixed adhesive powder.

Spray coating amount by one spray-coating operation using the above powder spray device is 20 to 50 mg/cm$^2$, and more preferably 25 to 50 mg/cm$^2$. According to specific experimental results, it was indicated as follows. With an application amount of less than 25 mg/cm$^2$, unevenness was likely to occur on spray-coated surface, and portions not completely covered by the mixed adhesive powder were likely to occur. In addition, at a time the physiological saline solution was dropped, gel formation was partially insufficient in some cases. On the other hand, when the spray-coating amount was 25 to 50 mg/cm$^2$, the entire coated surface was white and uniformly covered with the mixed adhesive powder. On contrary, with the spray-coating amount of more than 50 mg/cm$^2$, although the entire coated surface was white by being covered with the mixed adhesive powder, unevenness occurred in some spots. In particular, the adhesive powder mixture as is sometimes remained partially or spot-wise even when the physiological saline solution was sufficiently dropped.

In the case where the spray-coating amount per unit area exceeds 50 mg/cm$^2$, the spray-coating operation by the above powder spraying apparatus should be step-wise repeated instead of spray-coating all at once. That is, it is preferable to produce a multi-layered gel by repeating the spray-coating operation two or more times. As a result of various animal evaluations, when to block a relatively severe air leak, such as an experimental air leak model using rabbit lungs, it was found to be required a spray-coating amount of 100 mg/cm$^2$ or more, or in a range of 150 to 200 mg/cm$^2$ for example.

When water is added to the adhesive powder mixture by the spray-coating and subsequent adding of saline or water as described above, a Schiff bond is formed between the aldehyde group of the aldehyde-modified glucan and the amino group of the amino group-containing polymer, and this forms a cross-linking point to form a hydrogel having a network structure.

The hydrogel-state cured adhesive produced by such a curing reaction preferably has an adhesion strength of 20 gf/cm$^2$ or more, more preferably 50 gf/cm$^2$ or more. Here, "gf" indicates a gram-force, or about 0.01N. When the adhesion strength is less than 20 gf/cm$^2$, not only the original purpose of adhesion of the living tissue may not be fulfilled, but also the adhesion may not withstand a flexible movement accompanying expansion and contraction of the living tissue. Here, the adhesion strength is a value measured by a peeling test using a tensile tester.

The hydrogel-state cured adhesive produced by such a curing reaction preferably has a pressure-resistant adhesion strength of 100 mmHg or more, more preferably 150 mmHg or more. When less than 100 mmHg, the adhesion may not withstand a flexible movement accompanying expansion and contraction of the living tissue. Here, the pressure-resistant adhesive strength is a value measured by a method of applying pressure to the closed needle hole.

The hydrogel-state cured adhesive layer or hydrogel-state resin produced by such a curing reaction is converted into a liquid state (a flowable sol state) by self-decomposition after elapsing a predetermined decomposition period. This liquefaction time is easily adjustable, particularly by adjusting the amount of aldehyde groups introduced per anhydrous glucose unit. In order to shorten the decomposition time, the degree of to-aldehyde conversion is preferably relatively low. For example, 0.2 to 0.4 aldehyde groups per anhydrous glucose unit are introduced. In order to control the decomposition time within a range of 1 to 2 weeks, it is preferable to introduce 0.26 to 0.3 aldehyde groups per anhydrous glucose unit, and to realize the self-decomposition in a short period of 2 to 3 days, it is preferable to introduce 0.2 to 0.25 aldehyde groups per glucose unit.

The cured hydrogel-state adhesive layer or hydrogel-state resin generated by such a curing reaction is converted into a liquid state (a flowable sol state) by self-decomposition after elapsing a designed liquefaction time. In other words, so long as being in a water-containing state, the cured adhesive layer or resin is naturally decomposed and converted to a liquid state even without undergoing enzymatic decomposition or the like in a living body. Therefore, in a living body, it can be absorbed or excreted promptly after a predetermined period elapses. The decomposition time based on the design may be arbitrarily set within a range from several hours to four months, usually from one day to one month, particularly from two days to two weeks.

In order to achieve good adhesion performance and self-decomposition of the cured adhesive in hydrated gel-state formed by such a curing reaction, it is required to adequately set a ratio of reactive amino acid groups remaining in the partially carboxylated poly-L-lysine as produced, to molar number of the original amino groups before the partial carboxylation. The ratio of the remaining amino groups needs to be 60 to 95%, preferably 70 to 93%, more preferably 87 to 93%.

The mechanism of self-decomposition is not clear, but, presumably, after the aldehyde group of the aldehyde-modified α-glucan binds to the amino group to form a Schiff base, Amadori rearrangement of the Schiff base promptly cleaves the adjacent α-glucoside bond so that the molecular weight was easily reduced.

The medical adhesive and the medical resin of the preferred embodiment may be used for various purposes, which includes: a living tissue adhesive, a tissue filler, a hemostatic agent, a vascular embolic agent, a sealant for aneurysms, a sealant, an adhesion inhibitor, and a carrier for a drug discharge system (DDS).

The two-component reactive adhesive for medical use of the present invention exhibits excellent properties such as adhesive strength, curability by gelation, and applicability with a powder spray device. In addition, an extent or rate of self-degradability and flexibility as suitable for living tissue may be arbitrarily adjusted.

BRIEF DESCRIPTION OF THE DRAWINGS

FIG. 1 is a right side view of a powder spray device (powder spray gun) according to one embodiment, with a right-side housing part removed;

FIG. 2 is a partial cross-sectional view showing an essential part of the powder spray device of FIG. 1, cut along an air flow path, in a standby state;

FIG. 3 is a partial cross-sectional view as in FIG. 2, in a state of spraying and application;

FIG. 4 is a partial sectional perspective view of powder supply part, which is same with that appeared as FIG. 2 in JP2016-63919A, of the powder spray device of FIG. 1;

FIG. 5 is a perspective view of a funnel member included in the powder spray device of FIG. 1, and is same with that appeared as FIG. 4 in JP2016-63919A;

FIG. 6 is a graph showing the relationship between the spray time and the spray amount when the spray speed is relatively high;

FIG. 7 is a graph showing the relationship between the spray time and the spray amount when the spray speed is relatively low;

FIG. 8 is a set of images showing the relationship between amount of spraying application by one application operation and showing such spray-coated surface;

FIG. 9 is a graph showing a relationship between a residual amino group ratio and adhesive strength;

FIG. 10 is a graph showing a relationship between a residual amino group ratio and a decomposition ratio;

FIG. 11 is a schematic view showing an apparatus for an in-vitro needle hole occlusion test;

FIG. 12 is a micrograph of an aldehyde dextran powder as a first reactant;

FIG. 13 is a micrograph of succinic anhydride-treated polylysine powder as a second reactant; and FIG. 14 is a micrograph of an adhesive powder mixture (Lydex (trade name)).

DETAILED DESCRIPTION

The powder spraying apparatus (powder spray gun) 10 according to the embodiment shown in FIGS. 1 to 5 includes: (i) a funnel member 1, onto upper part of which, a powder container 7 is attachable, or with upper part of which, a powder container 7 is integrally provided; (ii) first three-way joint 3, onto first opening 31 of which, a discharge port 11B at lower end of the funnel member 1 is connected; (iii) an air-current supply tube 41 and a discharge tube 42, which are respectively connected with second and third openings 32, 33, of the first three-way joint 3; (iv) a housing 5 for accommodating these members, onto which the funnel member 1 and the first three-way joint 3 are attached as shakable and swingable; (v) a vibration motor 2 provided on the funnel member 1, (vi) a bypass air-current tube 8 that branches out from the air current supply tube 41 and joins to the discharge tube 42 in a confluent manner as bypassing the first three-way joint 3; and (vii) an on-off switching mechanism 6 that switches to and from; a spray-coating state (on state), in which compressed gas is sent through a spray-coating current tube line 4 passing through the air-current supply tube 41, inside of the first three-way joint 3 and the discharge tube 42, and is also sent through the bypass air-current tube 8; from and to a standby state (off state) in which the compressed gas is sent only through the bypass air-current tube 8.

As described above, the provision of the bypass air-current tube 8 and the on-off switching mechanism 6 makes it possible to smoothly discharge powder having low bulk density, low fluidity and high hygroscopicity, and realize uniform coating. In particular, as described later, the on-off switching mechanism 6 keeps the compressed gas flowing through the bypass air-current tube 8 not only at the time of standby but also at the time of spray-coating, so that not only the powder mixture of the medical adhesive of the embodiment but also other powder having low bulk density, low fluidity and high hygroscopicity are able to be uniformly applied in a predetermined amount.

In the illustrated embodiment, the connection between the bypass air-current tube 8 and the discharge tube 42 is formed by the second three-way joint 81, while the connection between the bypass air-current tube 8 and the air-current supply tube 41 is formed by the third three-way joint 82. The second three-way joint 81 comprises an obtuse-angled portion 81C at upstream of the branch 81B to which the bypass air-current tube 8 is connected. By the obtuse-angled portion 81C, direction of air-current is switched from obliquely upward direction into an obliquely downward direction. By providing such an angled portion 81C, the feeding speed of the adhesive powder will become more uniform.

The powder spray device (powder spray gun) 10 of the embodiment shown in FIGS. 1 to 5 is largely same as the powder spray device of JP2016-63919A except for the structure related to the bypass air-current tube 8 and the on-off switching mechanism 6. In a specific embodiment, the second three-way joint 81 and the third three-way joint 82 are relatively rigid members formed of a material similar to that of the first three-way joint 3 described later. On the other hand, a spray-coating air-current tube line 4 (including the air-current supply tube 41 and the discharge tube 42) and the bypass air-current tube 8 are formed of flexible tubes having uniform inner diameter and uniform outer diameter and made of same material, except for regions of the three-way joints 3, 81 to 82 and the on-off switching mechanism 6. In the illustrated embodiment, the angle at which the main body 81A of the second three-way joint 81 bends (or changes direction) at the bent portion 81C is 100° to 130°. Further, same with this is the angle at which the branch 81B connects to the main body 81A of the second three-way joint 81 at downstream of the bent portion 81C. On the other hand, the angle of the third three-way joint 82 between the main body 82A extending straight and the branch 82B, to which the upstream end of the bypass air-current tube 8 connects, is 30° to 60°.

In the illustrated embodiment, the on-off switching mechanism 6 comprises: a trigger lever 61, a valve housing member 62, and a coil spring 63. The trigger lever 61 comprises: a finger rest 61C and a rod 61D extending into the housing 5 from the finger rest 61C. The distal end portion 61B of the rod 61D is engaged with an end portion of the coil spring 63. Tus, it is able to squeeze the trigger lever 61 against the force of the coil spring 63 by putting an index finger or the like onto the finger rest 61C. Then, when the squeezing is stopped, the coil spring 63 returns to the initial position. Meanwhile, the coil spring 63 is housed in a tube-shaped room formed by the plate-shaped ribs 52 in the housing 5. On the other hand, the rod 61D of the trigger lever 61 is slidably inserted into the cylindrical main body 62C of the valve housing member 62. On the other hand, the valve housing member 62 comprises: a first air-flow tube section 62A inserted in the middle of the air-current supply tube 41 in a manner to intersect with the main body part 62C; and a second air-flow tube part inserted in the middle of the bypass air-current tube 8. Namely, the upstream part 41A of the air-current supply tube 41 is connected to the lower part of the first air-flow tube part 62A, and the downstream part 41B of the air-current supply tube 41 is connected to the upper section of the first air-flow tube section 62A. Further, the upstream part 8A of the bypass air-current tube 8 is connected to the lower portion of the second air-flow tube section 62B, and the downstream part 8B of the bypass air-current tube 8 is connected to the upper portion of the second air-flow tube section 62B.

The rod 61D of the trigger lever 61 has a first valve hole 61A on distal-end side and a second valve hole 61B on proximal-end side or on a part nearer to the finger rest 61C. The first valve hole 61A has a dimension L1 along axial direction of the rod 61D, which is substantially same as or slightly larger than the inner diameter D1 of the air-current supply tube 41 and the discharge tube 42. The first valve hole 61A is shaped as circular for example, as viewed from a direction of the air current. On the other hand, the dimension L2 of the second valve hole 61B along the axial direction of the rod 61D is equal to or slightly larger than a sum of the inner diameter D2 of the bypass air-current tube 8, and a stroke of the trigger lever 61, which is a moving distance at a time of squeezing and returning.

As shown in FIG. 2, in the initial position before the trigger lever 61 is squeezed, the first valve hole 61A of the trigger lever 61 is located between the first air-flow tube section 62A and the second air-flow tube section 62B, and does not contribute to supply of compressed air. The flow path in the first air-flow tube section 62A is closed. On the other hand, at this initial position, distal-end portion of the second valve hole 62B coincides with the flow path in the second air-flow tube section 62B. Thus, at the initial position, the compressed air is sent only through the flow path of the bypass air-current tube 8.

Next, as shown in FIG. 3, when the trigger lever 61 is squeezed up to a limit of such squeezing, the valve hole 61A matches the flow path in the first air-flow tube section 62A of the valve housing member 62, and thus the compressed air is sent through the air-current supply tube 41. At this spray-coating position, proximal-end portion of the second valve hole 64 coincides with the flow path in the second air-flow tube section 62B. In this way, at the spray-coating position, the compressed air is sent not only through spray-coating air-current tube line 4 as passing through the inside of the first three-way joint 3 but also through the bypass air-current tube 8. On the other hand, at beginning of squeezing the trigger lever 61, the switch projection 61E, which is provided at distal end of the rod 61D, swings up the hinge lever 21A of the switch element 21 to push the button 21B. Then, electric power from the battery 22 (a button battery in a specific example) in the battery box 55 is supplied to the vibration motor 2 through the power wiring 23 to perform vibration. Thus, by starting the vibration before supplying the compressed air, it is able to smoothly discharge the powder.

The upstream part 41A of the air-current supply tube 41 is connected to proximal-end portion 43 of the air-current supply tube line 4 via a straight tubular main body 82A of the third three-way joint 82. The proximal-end portion 43 is connected to the outlet of a sterile filtration unit 47 shaped as a disc (for example, a HEPA filter made of glass fiber filter paper). The compressed air supply tube is connected to the inlet of the sterilization filter unit 47. The upstream part 8A of the bypass air-current tube 8 is connected to the branch 82B of the third three-way joint 82. The compressed air supply tube is a flexible tube made of polyethylene or the like. For example, the compressed air supply tube is connected to a compressed air pipe in a wall through a wall connection port 46 and a pressure regulator 49 attached on the wall of the treatment room. The housing 5 includes a left-side housing part 5A and a right-side housing part (not shown), which are separately manufactured and are assembled to each other by the claws 53 so as to sandwich the funnel member 1, the three-way joint 3, and the spray-coating air-current tube 4 (which includes air-current supply tube 41 and the discharge tube 42), the bypass air-current tube 8, the nozzle 45, the trigger lever 61, and the like.

The nozzle 45 is a thin tube that extends linearly and is made of a rigid resin or metal. In the example shown in the figure, a nozzle tip tube 44 made of silicone rubber or the like is attached to the tip of the nozzle 45. The nozzle 45 is detachable and attachable to the main body of the powder spraying device 10 at the time of use, and a nozzle having a different length can be used according to a specific use situation. For endoscopic surgery, it is adoptable those having a length of 15 cm to 40 cm, for example, of 30 cm, and having an outer diameter of 3 mm to 7 mm, for example, of about 5 mm.

In order to use the adhesive or a sealant for a living tissue, the tip of the nozzle 45 is exposed to a high humidity environment. However, the powder spray device (powder spray gun) 10 of the present embodiment has a structure in which compressed air is sent through the bypass air-current tube 8 even during standby, so that occurrence of clogging within the powder discharging path including inside of the nozzle 45 is prevented. In present application, the term of "air" encompasses nitrogen or other gases.

In particular, the powder spray device 10 of the present embodiment has a structure in which compressed air is constantly sent through the bypass air-current tube 8 during spray-coating and standby. However, the flow rate of the compressed air at the time of spray-coating is larger in the spray-coating air-current tube line 4 than in the bypass air-current tube 8. Preferably, during the spray-coating, the flow rate through the bypass air-current tube 8 is 20 to 70%, or 30 to 60%, for example, 40 to 60% of the flow rate through the spray-coating air-current tube line 4. In the illustrated example, the inner diameter of the flexible tube forming the bypass air-current tube 8 and the inner diameter of the flexible tube 4 forming the air-current supply tube 41 and the discharge tube 42 are the same. However, it is considered that the flow rate of the flow path passing through the bypass air-current tube 8 is smaller than that of the spray-coating air-current tube line 4 due to, for example, bending in the third three-way joint 82. Because the compressed air also flows through the bypass air-current tube 8 during the spray-coating, the amount of the adhesive powder mixture to be discharged is decreased as compared with the case where the compressed air is not sent through the bypass air-current tube 8. However, when the experiment was conducted under the condition of spraying about 0.1 to 0.2 g per second, the spray amount was decreased by only about 30% as compared with the case where the bypass air-current tube 8 was closed up, at the time of spray-coating. On the other hand, when the bypass air-current tube 8 was closed up at the time of spray-coating, when squeezing of the trigger lever 61 was stopped to close up the spray-coating air-current tube line 4; just after such close up, the adhesive powder mixture was continuously sent out from the nozzle even though for a short time. However, in the case of the powder spray device 10 of the present embodiment, the discharge of the powder was fully stopped at the moment when the squeezing of the trigger lever 61 was stopped. This is presumably because the pressure in the second three-way joint 81 becomes higher than the pressure in the discharge tube 42 due to the pressure from the bypass air-current tube 8. As described above, the powder spray device 10 of the present embodiment enables the spray-coating of a predetermined amount of powder having low bulk density, low fluidity and high hygroscopicity. In particular, at a time of surgery, it is achievable a spray-coating of a predetermined amount of powder during a predetermined time, only by squeezing the trigger lever 61 with one hand.

Except for the parts described above, the powder spray device (powder spray gun) 10 of the present embodiment is largely same as that described in JP2016-63919A.

The powder spraying device 10 in the embodiment shown in the drawings is a pistol type powder spray gun, and utilizes compressed air from a compressed air pipe 46 to send out powder at inside of a vial 7, which is mounted upside down on the upper end of the powder spraying device 10 as sprayed from the nozzle 45 at the front end of the device 10. The vial 7 has a capacity of, for example, 3 to 50 mL, and in one specific example, of 7 mL, while the inner diameter of the bottle mouth 71 is, for example, 3 to 25 mm, and in one specific example, 6 mm. Except for the vial 7, the nozzle 45 and the compressed air supply tube 43, almost all the elements are housed in the housing 5. A rear part of the housing 5 is a handle 54, in which a battery box 55 is housed. The on-off switching mechanism 6 for supplying and shutting off compressed air is provided at an upper portion of the handle 54, and the air-current is supplied only while the trigger lever 61 corresponding to a trigger of a pistol is being pulled or squeezed. When the trigger lever 61 is lightly pulled, the vibration motor 2 starts operating through the switch element 21A. The vibrating motor 2 is housed in the pocket 12 of the funnel member 1, onto which the vial 7 is attached, so as not to be displaced, while the funnel member 1 and the three-way joint 3 connected to the lower end thereof are housed in the housing 5 as distanced with a play from the housing 5, in a manner to allow swinging and shaking. Therefore, when the vibration motor 2 is operated, the funnel member 1 as well as the vials 7 and the three-way joint 3, which are attached respectively to the upper and lower ends of the funnel member 1, are integrally vibrated vis-à-vis the housing 5. The first three-way joint 3 comprises; a part forming an air-current path 36; and a socket 34 connected to the lower end of the funnel member 1. The air-current path 36 forms a part of the spray-coating air-current tube line 4, as inserted between the on-off switching mechanism 6 and the nozzle 45, and more particularly, at between downstream end portion of the air-current supply tube 41 and the discharge tube 42. In this way, the powder dispersed in the air-current at the center of the three-way joint 3 is sent out from the nozzle 45. The downstream part 41B of the air-current supply tube 41 and the discharge tube 42 may be made of urethane rubber having excellent followability to vibration. However, a silicone tube or a PVC tube (in particular, a non-phthalic acid-based soft vinyl chloride resin) may be used. In addition, the upstream part 41A of the air-current supply tube 41 and the bypass supply tube 8 may also be formed by the same or similar flexible tube. In a specific example, the vibration motor 2 is that used for a manner mode of a mobile phone and has a diameter of 10 mm, a thickness of 3.3 to 3.5 mm, and a driving current of 50 to 70 mA at 3 V. Meanwhile, in a hospital room not equipped with the compressed air pipe 46, a compressor may be additionally provided to supply the compressed air into the powder spraying device 10.

The funnel member 1 comprises: a funnel body 11 that is entirely tapered; a pocket 12 that protrudes outward from the outer surface of the funnel body 11; and a mounting portion 13 that extends from the outer surface of the upper end 11D of the funnel body 11. The mounting portion 13 allows the vial 7 to be firmly fixed so as not to come off due to vibration, and the mounting opening 51 at the upper end of the housing 5 allows retaining of the funnel member 1 with a relatively large play. In the illustrated example, the mounting portion 13 of the funnel member 1 includes a flange 14 extending from a position slightly below the upper end of the funnel body 11 and a cylindrical portion 15 extending upward from the flange 14 at a site slightly inward from the outer peripheral end of the flange 14. The bottle mouth 71 of the vial 7 is inserted and fixed in a circular ring-shaped groove or gutter 17 formed by the upper end 11D of the funnel main body 11, the flange 14, and the cylinder 15. In order to prevent the vial 7 from coming off, a plurality of latching projections 16 are provided on the inner peripheral surface of the cylindrical portion 15.

On the other hand, the mounting opening 51 at the upper end of the housing 5 includes a cylindrical portion 51B protruding upward from the upper end of the housing 5, and upper and lower inward flanges 51A and 51C extending from the upper and lower ends of the cylindrical portion 51B. The movable range of the funnel member 1 is limited by vertically abutting the flange portion 14 of the funnel member 1 on the upper and lower inward flanges 51A and 51C. On the other hand, the limitation of the movable range in the horizontal direction is made in a manner that: the flange portion 14 is abutted against the cylindrical portion 51B of the mounting opening 51; and the cylindrical portion 15 of the funnel member 1 is abutted against the upper inward flange 51A. In the illustrated example, the movable range can be further limited by the lower inward flange 51C abutting against the step 18 on the lower surface of the flange 14. In one specific example, the movable range of the funnel member 1 is 3 mm vertically, and 2 mm horizontally at upper and lower ends of the funnel member 1.

The funnel member 1 is integrally formed by injection molding of a polypropylene resin. At this time, the mold surface corresponding to the inner surface of the funnel body 11 is subjected to mirror finishing. Thus, the JIS surface roughness Ra of the inner surface of the funnel body 11 was set to about 10 (nm). In the illustrated example, the taper angle (the angle with respect to the center axis 11C) of the inner surface of the funnel body 11 is about 10 degrees.

The pocket 12 of the funnel member 1 is formed so that the coin-shaped vibration motor 2 is tightly fitted in the pocket 12 after being pushed in. In such state, the rotation shaft 2A of the vibration motor 2 is disposed so that an extension of the rotation shaft 2A intersects with the central axis 11C of the funnel body 11. In the illustrated example, the position of the intersection coincides with equally dividing point of the height dimension of the funnel body 11. The pocket 12 has an opening 12A that opens to one side in the circumferential direction of the funnel body 11, and the vibration motor 2 is pushed in from the opening 12A. After such pushing in, for example, terminal portion protruding from the opening 12A as protruded from the peripheral surface of the vibration motor 2 is fixed onto outer surface of the funnel main body 11 or onto outer surface of the pocket 12, by attaching a strong adhesive tape. For example, a single-sided adhesive tape may be attached so as to cover the terminal portion of the vibration motor 2. In this way, it is possible to further prevent the displacement and dropout of the vibration motor 2 by using the adhesive tape. On the other hand, a strong double-sided adhesive tape may be arranged between the vibration motor 2 and the inner surface of the pocket 12. For example, a portion in the pocket 12 opposite to the opening 12A, or, the pocket bottom 12B may be shaped as a semicircle when viewed from a direction of rotation axis 2A of the vibration motor 2, and when the vibration motor 2 is pushed in. If so, a strong double-sided adhesive tape may be arranged as sandwiched between curved wall surface on the pocket bottom 12B and the peripheral surface of the coin-shaped vibration motor 2.

In the illustrated example, the lower end portion 11A of the funnel body 11 is pushed into the socket 34 that branches out upward from the center of the three-way joint 3 until lower end of the pocket 12 substantially contacts the upper end of the socket 34 so that the funnel body 11 is firmly connected to the three-way joint 3. On the other hand, the lower end outlet 11B of the funnel main body 11 is connected to the first opening 31 provided at the bottom of the socket 34 so that the inner peripheral surfaces thereof are continuous. In particular, the first opening 31 is provided so as to form an opening in a tube wall of the air-current tube line 36 in the three-way joint 3. Therefore, the lower end outlet 11B of the funnel main body 11 extends to a position almost in contact with the air-current tube line 36. On the other hand, in the illustrated example, a curved-in recess 35 is provided on bottom surface of a junction 37, which is a location facing the first opening 31, on the tube wall of the air-current tube line 36.

As shown in FIGS. 1 to 3, the outer surface of the three-way joint 3 is abutted against the plate-shaped ribs 52 protruding from the inner surface of the housing 5, so that the three-way joint 3 and the lower portion of the funnel member 1 are held and the movable range is limited. In the illustrated example, the upper end of the socket portion 34 of the three-way joint 3 is located in an opening 52A of the horizontal plate-shaped rib, and may be abutted against the edge of the opening 52A. In addition, the projection at the lower end of the three-way joint 3 is located in an opening 52B of another horizontal plate-shaped rib, and may abut on the edge of the opening 52B. In the initial position, the lower end of the three-way joint 3 is placed and supported on the periphery of the opening 52B of the horizontal plate-shaped rib.

Hereinafter, the medical two-component reactive adhesive according to one embodiment will be described.

1. Preparation of Powdered Aldehyde Dextran (First Reactant; AD)

400 g of dextran having a molecular weight of 70,000 (Meito Sangyo Co., Ltd., "Dextran 70") is dissolved in 1600 ml of ion-exchanged water; and 50 g of sodium periodate (molecular weight of 213.89) is dissolved in 800 ml of ion-exchanged water was added thereto, and reacted while stirring in a 50° C. water bath for 3 hours. Then, the solution after the reaction was dialyzed, filtered with a 0.45 µm filter, and dried. Further, a pulverization was performed using a small pulverizer (Wonder Crush Mill D3V-10, Osaka Chemical Co., Ltd.) to obtain a powdery aldehyde dextran (2.5/20). Here, "(2.5/20)" indicates the charging ratio of sodium periodate to "Dextran 70" for forming the aldehyde dextran. In the obtained aldehyde dextran, the introduction amount of aldehyde group per sugar residue amount (mole) was 0.28. The amount of the aldehyde group introduced was measured by a redox titration method. Specifically, 20 ml of a 0.05 mol/L aqueous iodine solution, 10 ml of a 10 mg/ml aqueous aldehyde dextran solution, and 20 ml of a 1 mol/L aqueous sodium hydroxide solution were placed into a 100 ml Meyer flask and stirred at 25° C. for 15 minutes. Then, 15 ml of a 6 v/v % aqueous sulfuric acid solution was added, and titration was performed with a 0.1 mol/L aqueous sodium thiosulfate solution. The end point was when the reaction system became colorless and transparent, and the indicator was an aqueous starch solution.

When the particle size of the powder was evaluated using a stereomicroscope, the average particle size was 90 µm as shown in the photograph of FIG. 12. Furthermore, as a result of observing the surface properties with an electron microscope, it was found to be porous. The average aspect ratio (ratio of the major axis to the minor axis) was about 1.6.

2. Preparation of Succinic Anhydride-Treated Polylysine (Second Reactant; SAPL)

10 g of succinic anhydride (Nacalai Tesque) was added to 400 g of a 25% by weight ε-polylysine aqueous solution (molecular weight: 4,000; JNC (Chisso) Corporation) and reacted at 50° C. for 1 hour. The solution after the reaction was filtered through a 0.45 µm filter and dried. Further, a pulverization treatment was performed using a small pulverizer (Wonder Crush Mill D3V-10, Osaka Chemical Co., Ltd.) to obtain a powdery succinic anhydride-treated polylysine.

With respect to the obtained succinic anhydride-treated polylysine, the residual ratio of free amino groups (side chain and terminal amino groups not involved in the formation of peptide bonds) was determined to be 89.5%. For this measurement, after dissolving in water, a ninhydrin solution and an acetic acid/sodium acetate buffer solution having a pH of 5.5 were added, heated in a boiling water bath for 3 minutes, and quenched to obtain a sample solution. Then, a test was conducted according to the method of measuring ultraviolet-visible-range absorbance according to the Japanese Pharmacopoeia. In particular, the absorbance at a wavelength of 570 nm was measured, and the amino group content in the sample solution was determined.

The obtained powdery succinic anhydride-treated polylysine was evaluated using a stereoscopic microscope in the same manner as in the case of the above-mentioned aldehyde dextran. As shown in FIG. 13, random-shaped porous powder almost same to the photograph of FIG. 12 was obtained. Further, the average particle size was 80 µm. The average aspect ratio was about 1.7.

3. Mixed Adhesive Powder

The mixed adhesive powder (average particle size of 80 µm) obtained by mixing the above powdery aldehyde dextran and powdery succinic anhydride-treated polylysine in a weight ratio of 4/1 has a molar ratio of aldehyde group to amino group, which is almost "1" (one). FIG. 14 shows the obtained mixed adhesive powder. The bulk density of the mixed adhesive powder was 420 mg/cm$^3$. The mixed adhesive powder is charged into a 7-mL glass vial with an aluminum cap by 3 g each, and by sealing the cap, stored as sealed to keep a water content of 1.0% or less, particularly of 0.5 to 1.0%. In the present application, this mixed adhesive powder is also referred to as "Lydex (registered trademark)" as appropriate. Unless otherwise specified, those having the above-mentioned reaction charge ratio and mixing ratio were used. That is, a mixed adhesive powder ("Lydex powder 2.5/20") as obtained as below was adopted; water succinic acid-treated polylysine obtained by reacting 10 g of succinic anhydride with 100 g of ε-polylysine was used, and the charge ratio of sodium periodate to "Dextran 70" for aldehyde conversion of dextran was set to 2.5/20; and then the aldehyde dextran (AD) and succinic anhydride-treated polylysine (SAPL) were mixed at a weight ratio of 4/1.

4. Spray-Coating Mixed Adhesive Powder

The mixed adhesive powder was applied using the powder spray device (powder spray gun) 10 shown in FIGS. 1-5. At this time, the nozzle 45 was connected to the powder spraying apparatus main body 10A, the compressed air supply pipe 43 (air supply tube) was attached to the sterilization filter 47 on the proximal side, and the pressure regulator 49 was connected. Further, the vial bottle 7 filled with the mixed adhesive powder in which the first reactant and the second reactant were previously mixed was turned upside down and connected to the powder spray device main body 10A. The pressure-adjusted compressed air passes through the sterilization filter 47 and is supplied to the measuring section (inside the first three-way joint 3) connected to the vial bottle 7. In this measuring section, the mixed adhesive powder is further mixed by compressed air; and is sent out through the nozzle 45. Using such a powder spray device 10, the mixed adhesive powder was directly sprayed and applied to a portion wetted by a body fluid, blood or the like. Next, using a "mist adapter" (Maeda Sangyo Co., Ltd.: spray nozzle) at the tip of the syringe that sucked the saline solution, spray the saline solution evenly until the mixed adhesive powder gels uniformly and transparently; and then allowed to stand for 2 minutes.

The pressure of the compressed air at the wall connection was 4 atm. (about 400 kPa). The spray speed can be adjusted by adjusting the pressure supplied to the compressed air supply pipe 43 by the pressure regulator 49. As a result of repeating the spraying experiment, it was considered that 0.1 to 0.8 g (100 to 800 mg) per second was optimal for uniformly applying a predetermined amount.

5. Spray Speed

As shown in FIGS. 6 and 7, the spraying speed was adjusted to two stages of 0.25 g/sec (FIG. 6) and 0.75 g/sec (FIG. 7), and relationship between the spraying time and the total spraying amount (from the start of spraying) were investigated. In FIGS. 6 and 7, squares (upright large squares) indicate the case where the driving current of the vibration motor 2 was set at a maximum of 70 mA, while rhombuses (small squares that are tilted 45 degrees) indicated those set at a minimum of 50 mA. As a result, it was confirmed that as long as the drive current of the vibration motor 2 was large enough, the spray state was stable regardless of the spray speed, and that the spray could be performed quantitatively within a predetermined time.

6. Application Amount by a Single Spray-Coating Operation and Sealant Performance Test Using Rabbit Lung Experimental Air Leak Model After resection at the maximum part of the left posterior lobe of the left lung of a Japanese white male rabbit, declamping was performed, the inspiratory pressure was increased to 30 cmH$_2$O, and physiological saline was dropped on the cut lung surface to confirm that there was air leakage. When the number of leak points was less than four, the disposable injection needle 18 G was punctured in a direction perpendicular to the cut surface, and a leak model was prepared so that the leak points were four or more in total. Then, it was confirmed that there was air leakage as described above.

Next, using the powder spray device (powder spray gun) 10 shown in FIGS. 1 to 5, the spray-coated amount (the amount of the powder adhesive per area of the area to be bonded) by a single spray-coating operation was varied; and in such a way, the spray-coating is made to a circular area having a diameter of 30 mm including the above-mentioned four or more air leak points. This circular area is an area corresponding to the air leak model described above, and is an area that is wetted by body fluids. Immediately after the application of the mixed adhesive powder, an amount of physiological saline just to be sucked by the mixed adhesive powder was dripped evenly to the area. FIG. 8 shows a series of photographs embedded in a table. These series of photographs show, for each application amount, how are the spray-coated surfaces immediately after such application, and at 2 minutes after the saline solution was dropped so as to be gelated. As shown in FIG. 8, when the applied amount was less than 25 mg/cm$^2$, there was unevenness on the applied surface, and there was a portion that was not completely covered with the mixed adhesive powder. Then, even after the physiological saline was sprayed and allowed to stand for 2 minutes, there appeared to be portions where the formation of the hydrogel was insufficient.

On the other hand, FIG. 8 shows the result of measuring the maximum pressure (burst pressure) that can prevent air leakage when sealing is performed with each application amount per area in the needle hole occlusion test. For this measurement, a ventilator was attached to the left posterior lobe of the left lung of the rabbit that formed the air leak model. After 2 minutes or 5 minutes, a load of about 90 mmHg (about 27 cmH$_2$O) is applied as an initial pressure, and after confirming that there is no leakage from the needle hole, a load is applied at a speed of 150 mL/hr., and leakage is performed from the needle hole. The pressure-resistant adhesive strength (mmHg) at this time was determined.

As a result, as shown in FIG. 7, the highest burst pressure was obtained when the amount of a single spray-coating operation was 45 mg/cm$^2$, and the burst pressure was somewhat high even at 25 mg/cm$^2$. On the other hand, when the amount of a single spray-coating operation was 11 mg/cm$^2$ and when the amount was 77 mg/cm$^2$, the burst pressures was significantly lower.

From these results, it has been known that when applying a large amount exceeding 50 mg/cm$^2$, the application operation by spraying should be repeated instead of applying at once. That is, it has been known that a multi-layered gel should be produced by performing the coating operation twice or more times. In animal evaluation, a relatively severe air leak such as a rabbit lung experimental air leak model may require an application amount of 100 mg/cm$^2$ or more. Resultantly, the application amount per unit area after completion of the application operation was basically set in a range of 50 to 100 mg/cm$^2$ and was increased, if necessary or appropriate, to 150 mg/cm$^2$ for example.

7. Adhesion Performance and Decomposability as Dependent to Residual Amino Group Ratio of Succinic Anhydride-Treated Polylysine Prepared in the same manner as in "2. Preparation of succinic anhydride-treated polylysine (second reactant)" above, except that 400 g of a 25 wt % ε-polylysine aqueous solution (molecular weight: 4,000, JNC (Chisso) Corporation) was added by varied amounts of succinic anhydride (Nacalai Tesque) in a range of 6 g to 14 g, namely, at 5 levels—6 g, 8 g, 10 g, 12 g, and 14 g so as to carry out a reaction and to obtain a powdered succinic anhydride-treated polylysine having 5 levels of the residual amino group ratio. As a result, succinic anhydride-treated polylysines having the residual amino group ratios of 75.8 to 89.5% were obtained. Similarly, by adding succinic anhydride (Nacalai Tesque) in a range of no more than 60 g was added to 400 g of a 25% by weight aqueous solution of ε-polylysine (molecular weight: 4,000, Chisso Corporation), the residual amino group ratio was further greatly changed in obtaining a powdery succinic anhydride-treated polylysine. In addition, the quantification of the residual amino group ratio was performed as follows. First, the powdery succinic anhydride-treated polylysine was dried and dissolved in water; then, added by a ninhydrin solution and an acetic acid/sodium acetate buffer solution having a pH of 5.5; and heated in a boiling water bath for 3 minutes, and quenched to obtain a sample solution. Then, a test was conducted according to the method of measuring ultraviolet-visible absorbance of the Japanese Pharmacopoeia, the absorbance at a wavelength of 570 nm was measured, and the amino group content in the sample solution was determined.

The above powdery aldehyde dextran and 5 levels of powdery succinic anhydride-treated polylysine were mixed at a weight ratio of 4/1. Such mixed adhesive powder in an amount of 3 g was charged into each of 7 mL vials using a filling machine.

<Adhesive Strength by In Vitro Peel Test>

A stainless steel jig having an inner diameter of 15 mm was placed on the collagen casing having been wiped with ethanol, and 50 mg of Lydex mixed adhesive powder was placed into the jig. The mixture was spread with a microspatula to a uniform thickness, and then 150 μL of physiological saline was added. A saline solution was added to thus obtained gel. After 2 minutes, the stainless steel jig was lifted at a speed of 10 mm/min by a tensile tester (Tensilon Universal Tester RTC-1210A, Orientec Co., Ltd.), and the applied load at the time of peeling from the collagen casing was taken as the adhesive strength. The results are shown in Table 1, FIG. 9 and Table 2.

As shown in Table 1 and FIG. 9, when the residual amino group ratio was about 90%, the adhesive force was considered to be the largest. However, even when the residual amino group ratio was changed in the range of 70 to 86%, no remarkable difference was observed in the adhesive strength. When the residual amino group ratio was less than 70% or greater than about 90%, no good hydrogel was formed, and no measurable adhesive strength was obtained.

<In Vitro Gel Decomposition Test>

A dialysis membrane (dialysis membrane 36/32, model number: UC36-32-500, Edia Co., Ltd.) is cut into a rectangle of about 5 cm, washed with tap water, dewatered to remove water, and one side of the dialysis membrane is wiped with ethanol. This is to be referred as a collagen casing wiped with ethanol. A stainless steel jig having an inner diameter of 15 mm was placed on the collagen casing, and 40 mg of a mixed adhesive powder of Lydex was placed therein. The mixture was spread with a microspatula so as to have a uniform thickness; and then added by 120 μL of saline so as to be gelated. The gelled Lydex is immersed in a sealed container containing 50 mL of physiological saline, and placed in an extra-mini-size constant temperature shaking incubator "Bioshaker" (Model V-BR-36, Taitec Co., Ltd.) set at 37° C. Then, it was shaken at 100 rpm. After 6 hours and 22 hours, the disappearance ratio of gelled Lydex was visually confirmed. Table 1 and FIG. 9 and Table 2 show the results.

Decomposition of Lydex resins containing succinic anhydride-treated polylysines having different residual amino group ratios was, for each of the ratios, in a level of about 50% vanishing after 6 hours, and about 90% vanishing after 22 hours. It was confirmed that the level of the decomposition was almost same even when the ratio was changed in a range of 70 to about 90%. However, outside of this range, the formation of the hydrogel itself was insufficient as described above.

TABLE 1

| | Residual amino group ratio (%) of succinic anhydride-treated polylysine | | | | |
|---|---|---|---|---|---|
| | 75.8 | 79.8 | 84.7 | 86.0 | 89.5 |
| Average particle size of Lydex powder (μm) | 57.8 | 70.6 | 70.1 | 65.0 | 66.5 |
| Adhesive strength by in vitro peel test (gf/cm$^2$) | 117.9 ± 20.6 | 121.1 ± 21.3 | 123.3 ± 17.2 | 114.3 ± 13.7 | 142.4 ± 29.0 |
| In vitro gel degradation test (37° C. physiological saline, shaking): Decomposition rate after 22 hours (%) | 90 | 90 | 90 | 90 | 90 |

TABLE 2

| | Residual amino group ratio (%) of succinic anhydride-treated polylysine | | | | | | | | |
|---|---|---|---|---|---|---|---|---|---|
| | 35.6 | 65.0 | 70.0 | 75.8 | 79.8 | 84.7 | 89.5 | 95.0 | 100 |
| Properties of succinic anhydride-treated polylysine powder * 1 | ○ | ○ | ○ | ○ | ○ | ○ | ○ | Δ | X |
| Gel formation from Lydex powder * 2 | X | Δ | ○ | ○ | ○ | ○ | ○ | — | — |
| Lydex gel adhesive strength * 3 | — | — | ○ | ○ | ○ | ○ | ◎ | — | — |

TABLE 2-continued

Residual amino group ratio (%) of succinic anhydride-treated polylysine

| | 35.6 | 65.0 | 70.0 | 75.8 | 79.8 | 84.7 | 89.5 | 95.0 | 100 |
|---|---|---|---|---|---|---|---|---|---|
| Degradability of Lydex gel * 4 | — | — | ○ | ○ | ○ | ○ | ○ | — | — |

* 1 ○: No problem in mixing with aldehyde dextran to prepare Lydex powder. X: Hydration and cohesion of the powder were large, and a Lydex powder would not be prepared. Δ: Intermediate between these two.
* 2 ○: When moisture is added to Lydex powder, it was able to be gelled without any problem. X: No gel is formed even when water is added dropwise. Δ: Intermediate between these two.
* 3 ○: 100 gf/cm² or more, which is a practical adhesive strength.
* 4 ○: Decomposition rate of 90% or more after 24 hours.

8. Adhesion Performance and Decomposability as Dependent to Aldehyde Group Introduction Amount Prepared in the same manner as in the above "Preparation of powdered aldehyde dextran (first reactant)", except that the amount of sodium periodate added to 400 g of dextran and reacted was changed to 60 g (charge ratio 3.0/20) and 80 g (charge ratio 4.0/20). In this way, 0.30 and 0.39 aldehyde groups were introduced per anhydroglucose unit, respectively. Similarly to the above, aldehyde dextran and powdered succinic anhydride-treated polylysine were mixed at a weight ratio of 4/1 to obtain a mixed adhesive powder.

An in vitro gel degradation test was performed in the same manner as in the above "7.". The gel disappeared in 2-3 days when the amount of aldehyde group introduced was 0.27 ("Lydex powder 2.5/20"); and the gel disappeared in 7 to 11 days when the amount of introduced aldehyde groups is 0.30 ("Lydex powder 3.0/20"; and the gel disappeared. When the amount of aldehyde group introduced was 0.39 ("Lydex powder 4.0/20"), no significant change was observed at a time the Lydex powder (3.0/20) has disappeared, and it is presumed that it would take 4 weeks or more. As is known from the results, the amount of aldehyde groups introduced is able to be reduced by reducing the amount of sodium periodate, so that cross-linking due to Schiff bonds with succinic anhydride-treated polylysine is reduced, and the gel disappears. In this way, disappearance of the gel can be accelerated and the decomposition time of the gel can be adjusted arbitrarily.

Even when the amount of the aldehyde group introduced was changed, no significant difference was found in the adhesive strength measured in the same manner as in "6." and the pressure resistance measured by the needle hole blocking test.

FIG. 11 shows a schematic diagram of an apparatus used for the needle hole occlusion test. First, a stainless steel jig having an inner diameter of 15 mm was placed on a collagen casing wiped with ethanol, and a hole was made in the center with an 18 G needle. Then, 50 mg of the mixed adhesive powder of Lydex was put into the needle hole portion, spread with a spatula so as to have a uniform thickness, and then gelled by adding 150 μL of a physiological saline solution. After 2 minutes or 5 minutes, a load of about 90 mmHg was applied as an initial pressure, and after confirming that there was no leakage from the needle hole, a load was applied at a speed of 150 mL/hr; and the pressure when leaking from the needle hole started was determined as adhesive strength (mmHg).

TABLE 3

| | Lydex powder (2.5/20) | Lydex powder (3.0/20) | Lydex powder (4.0/20) |
|---|---|---|---|
| Amount (g) of sodium periodate per 20 g of Dextran 70 | 2.5 | 3.0 | 4.0 |
| Aldehyde group introduction amount per anhydroglucose unit (mol/glucose unit) | 0.27 | 0.30 | 0.39 |
| in vitro Gel degradation test (37° C. physiological saline, shaking) | 2 to 3 days | 7 to 11 days | More than 4 weeks |
| in vitro Adhesion strength by peel test (gf/cm²) | 73 ± 19 | (40 ± 6) | 64 ± 18 |
| in vitro Pressure-resistant adhesive strength by needle hole closure test (mmHg) | 243 ± 53 | (300 ± 1) | 236 ± 23 |

9. Effect of Gel Thickness on Gel Vanishing Time

The abdominal skin of a 7-week-old male rat was incised by 2-3 cm along the median line from the vicinity of the sternal xiphoid so as to expose the liver, and a stainless steel jig (inner diameter 15 mm) was placed on the surface of the inner right lobe. The aforementioned "Lydex powder 2.5/20" or the Lydex powder "Lydex powder 4/20" was sprayed uniformly on the inside of the jig, and then a saline solution was sprayed to form a gel. The liver was returned to its original position, the incision was sutured, and the surgical field was cleaned. The application amount of the Lydex powder was three levels of 38 mg, 76 mg, and 114 mg, and the application thickness was 0.5 mm, 1 mm, and 1.5 mm, respectively. The coating thickness was calculated from the jig area and the bulk density of the Lydex powder (420 mg/cm³).

After 2 weeks, 4 weeks, 6 weeks, and 8 weeks, after thoracotomy, the liver was excised and the state of degradation was observed by visual inspection. Table 4 shows the results.

In the case of Lydex powder 2.5/20, only a slight residual gel was observed in the group applied with intermediate thickness (1 mm) and 2 weeks after the application, and no residual gel was observed in thinly spray-coated group (0.5 mm). At 4 weeks and 6 weeks after application, no gel remained even in thickly spray-coated group (1.5 mm), thus it was confirmed that the gel had disappeared promptly. On the other hand, in the case of the Lydex powder 4.0/20, gel remained even 8 weeks after application in the intermediately spray-coated group, and only a small amount of gel remained in the thinly spray-coated group. From the above, it was known that the influence of the gel thickness on the decomposition period was not significant.

TABLE 4

| Application category (Coating amount/ Coating thickness) | Lydex powder 2.5/20 | | | Lydex powder 4.0/20 | |
|---|---|---|---|---|---|
| | Thinly coated group (38 mg/0.5 mm) | Intermediately coated group (76 mg/1.0 mm) | Thickly coated group (114 mg/1.5 mm) | Thinly coated group (38 mg/0.5 mm) | Intermediately coated group (76 mg/1.0 mm) |
| $2^{nd}$ week | Vanished (n = 2) | Extremely slightly remained (n = 3) | | | |
| $4^{th}$ week | Vanished (n = 3) | Vanished (n = 3) | Vanished (n = 3) | | |
| $6^{th}$ week | Vanished (n = 3) | Vanished (n = 3) | Vanished (n = 3) | | |
| $8^{th}$ week | | | | Extremely slightly remained (n = 6) | Remained (n = 6) |

10. Occlusion Test on the Entire Cut Surface of the Lung Parenchyma

Example 1

The left posterior lobe of the left lung of a Japanese white male rabbit was cut at its maximum to form a cut plane of the lung parenchyma. Then, "Lydex powder 2.5/20" was sprayed on the cut surface of the lung parenchyma using the above powder spray device, and then a saline solution was sprayed to form a gel. Subsequently, the inspiratory pressure of the ventilator connected to the rear lobe of the left lung of the rabbit was gradually increased from 20 $cmH_2O$ to 50 $cmH_2O$, and the presence or absence of air leakage was confirmed. When air leak was observed under a certain intake pressure condition, no further pressurization was performed, and the intake pressure was adopted as the air leak occurrence intake pressure. Table 5 shows the results.

Example 2

"Lydex powder 4.0/20" was sprayed on the cut surface of the lung parenchyma using the above powder spray device, and then physiological saline was sprayed to gel. Subsequently, the same operation as described above was performed to check for air leaks. Table 5 shows the results.

Comparative Example 1

(4) The fibrin glue was applied to the whole cut surface of the lung parenchyma, as the mixture of liquids "A" and "B". Subsequently, the same operation as described above was performed to check for air leaks. Table 5 shows the results.

Comparative Example 2

Regarding the combined use of the fibrin glue and the PGA sheet-like suture reinforcing material, the fibrin glue "A" liquid was applied to the entire cut surface, and then the PGA sheet-shaped suture-reinforcing material cut into about 5 mm square was adhered to the air leak portion. Next, a mixture of the fibrin glue "A" liquid and the "B" liquid was applied to the entire cut surface and allowed to be mingled with a PGA sheet-shaped suture reinforcing material, and left for about 2 minutes. Subsequently, the same operation as described above was performed to check for air leaks. Table 5 shows the results.

As a result of confirming the sealant performance, no air leakage was observed even at an intake pressure of 50 $cmH_2O$ in only one instance of Example 1 (Lydex powder 2.5/20). In all other cases, air leaks were observed. The air pressure at which air leak occurred was: 30 to 40 $cmH_2O$ (average value: about 40 $cmH_2O$) in Example 1 (Lydex powder 2.5/20); 30-40 $cmH_2O$ (average value: 36 $cmH_2O$) in Example 2 (Lydex Powder 4.0/20); 20-40 $cmH_2O$ (average value: 30 $cmH_2O$) in Comparative Example 1 (fibrin glue); and 30-50 $cmH_2O$ (average: 38 $cmH_2O$) in Comparative Example 2 (a combination of PGA sheet-shaped suture reinforcing material and fibrin glue).

As a result of performing a Kruskal-Wallis test for the air pressure at which air leak occurred, Examples 1, 2 and Comparative Example 2 were almost equivalent. The Lydex powders of Example 1 and Example 2 exhibited sealant performance equal to or higher than that of Comparative Example 2, in which the combination of PGA sheet-like suture reinforcing material and fibrin glue is used).

TABLE 5

| | | Number of animals at each leak pressure | | | | Number of animals that did not show any air leak even with inspiratory pressure of 50 $cmH_2O$ |
|---|---|---|---|---|---|---|
| | Groups | 20 cm $H_2O$ | 30 cm $H_2O$ | 40 cm $H_2O$ | 50 cm $H_2O$ | |
| Example 1 | Lydex powder 2.5/20 | 0 | 1 | 3 | 0 | 1 |
| Example 2 | Lydex powder 4.0/20 | 0 | 2 | 3 | 0 | 0 |
| Comparative Ex. 1 | Fibrin glue | 1 | 3 | 1 | 0 | 0 |

TABLE 5-continued

|  | Groups | Number of animals at each leak pressure | | | | Number of animals that did not show any air leak even with inspiratory pressure of 50 cmH$_2$O |
|---|---|---|---|---|---|---|
|  |  | 20 cm H$_2$O | 30 cm H$_2$O | 40 cm H$_2$O | 50 cm H$_2$O |  |
| Comparative Ex. 2 | Combined use of PGA sheet reinforcement and fibrin glue | 0 | 2 | 2 | 1 | 0 |

11. Change in Adhesive Strength Depending on Mixing Ratio

By changing the mixing ratio of aldehyde dextran (AD), succinic acid-treated polylysine and (SAPL), the molar ratio of aldehyde groups to amino groups is changed from 5/1 to 5/5, and the above-mentioned "7.". The adhesion was measured by a peel test. The results are shown in Table 6 below. As is clear from Table 6 below, it was confirmed that the adhesive strength was highest when the reaction molar ratio was 1/1. Further, even if the reaction molar ratio was slightly deviated, the decrease in adhesive strength was not so large.

TABLE 6

| AD/SAPL | Adhesive strength (gr; gram force) |
|---|---|
| 5/1 | 58.88 |
| 5/2 | 81.20 |
| 5/3 | 100.15 |
| 5/4 | 102.70 |
| 5/5 | 110.12 |

The powder spray device of the present invention makes it possible to uniformly apply a predetermined amount of the medical adhesive of the present invention, or other powder having low bulk density and low fluidity and high hygroscopicity. The medical adhesive of the present invention is suitably used as a living-tissue adhesive, a tissue filler, a hemostatic agent, a vascular embolic agent, a sealant for an aneurysm, a sealant, an adhesion inhibitor, and a carrier for a drug delivery system (DDS).

What is claimed is:

1. A powder spray device comprising:
   a funnel member, onto an upper part of which, a powder container is attachable or the powder container is integrally provided;
   a first three-way joint having a first opening, a second opening and a third opening, the first opening connected to an outlet at a lower end of the funnel member;
   an air-current supply tube and a discharge tube respectively connected to the second and third openings of the first three-way joint;
   a vibration motor attached and fixed onto an outer surface of a funnel body of the funnel member;
   a bypass air-current tube that branches off from the air-current supply tube and is connected to the discharge tube; and
   a switching mechanism that switches from and to a standby state, in which compressed gas is sent only through the bypass air-current tube, and switches to and from a spray-coating state, in which compressed gas is sent out through a spray-coating air-current tube line including the air-current supply tube, inside of the three-way joint and the discharge tube, and also through the bypass air-current tube,
   the switching mechanism including a valve provided to the air-current supply tube and a trigger lever that opens and closes the valve, wherein when the trigger lever is squeezed by a user, the vibration motor starts a vibration motion before starting of sending out compressed gas through the air-current supply tube in the spray-coating state.

2. The powder spray device according to claim 1, further comprising
   a housing configured to house the funnel member, the first three-way joint, the air-current supply tube, the discharge tube, the vibration motor, the bypass air-current tube, and the switching mechanism, wherein
   the funnel member and the first three-way joint are attached to be shaken or swayed.

3. The powder spray device according to claim 1, further comprising:
   a second three-way joint that connects the bypass air-current tube and the discharge tube, the second three-way joint including a branch to which the bypass air-current tube is connected and an obtuse-angled portion disposed at an upstream of the branch so that in the obtuse-angled portion, an air-current direction is switched from an obliquely upward direction to an obliquely downward direction; and
   a third three-way joint that connects the bypass air-current tube and the air-current supply tube.

4. The powder spray device according to claim 1, wherein
   the funnel member includes a pocket or an attachment, which is integrally formed on the outer surface of the funnel body of the funnel member so that the vibration motor is fitted into the pocket or engages with the attachment.

5. The powder spray device according to claim 1, further comprising
   a valve housing, wherein
   the valve is formed by a portion of the trigger lever and a portion of the valve housing.

6. The powder spray device according to claim 1, wherein the three-way joint has an air-current tube line, an inner diameter of which is not larger than those of the air-current supply tube and the discharge tube.

7. A powder spray device comprising:
   a funnel member, onto an upper part of which, a powder container is attachable or the powder container is integrally provided;
   a first three-way joint having a first opening, a second opening and a third opening, the first opening connected to an outlet at a lower end of the funnel member;
   an air-current supply tube and a discharge tube respectively connected to the second and third openings of the first three-way joint;

a vibration motor attached and fixed onto an outer surface of a funnel body of the funnel member;

a bypass air-current tube that branches off from the air-current supply tube and is connected to the discharge tube; and a switching mechanism that switches from and to a standby state, in which compressed gas is sent only through the bypass air-current tube, and switches to and from a spray-coating state, in which compressed gas is sent out through a spray-coating air-current tube line including the air-current supply tube, inside of the three-way joint and the discharge tube, and also through the bypass air-current tube, wherein the switching mechanism includes a trigger lever including a rod having first and second valve holes respectively for the air-current supply tube and the bypass air-current tube, and a valve housing, into which the rod of the trigger lever is slidably inserted, the valve housing including first and second air-flow sections that are respectively interposed in the air-current supply tube and in the bypass air-current tube, so as to form a valve by a portion of the air-current supply tube, a portion of the trigger lever, and a portion of the valve housing.

8. The powder spray device according to claim 7, wherein a dimension of the second valve hole along the rod of the trigger lever is larger than a stroke of the trigger lever.

9. A spray-coating system comprising a powder spray device and adhesive powder, which is hygroscopic and includes random-shaped particles, the powder spray device including:

a funnel member, onto an upper part of which, a powder container accommodating the adhesive powder is attached or integrally provided;

a first three-way joint having a first opening, a second opening and a third opening, the first opening connected to an outlet at a lower end of the funnel member;

an air-current supply tube and a discharge tube respectively connected to the second and third openings of the first three-way joint; a vibration motor attached and fixed onto an outer surface of a funnel body of the funnel member;

a bypass air-current tube that branches off from the air-current supply tube and is connected to the discharge tube, a valve provided to the air-current supply tube; and a trigger lever that opens and closes the valve, wherein when the trigger lever is squeezed by a user, the vibration motor starts a vibration motion before starting of sending out compressed gas through the air-current supply tube in a spray-coating state.

10. The spray-coating system according to claim 9, wherein the random-shaped particles are porous and have an average particle diameter of 10-150 micrometers, and a water content of the adhesive powder is no more than 2.0%.

11. The spray-coating system according to claim 9, wherein the adhesive powder includes a first reactant comprised of powder of aldehyde-groups-introduced alpha-glucan having a weight-average molecular weight in a range of 1000 to 200,000, and a second reactant comprised of powder of partially carboxylated poly-L-lysine, which is obtainable by modifying poly-L-lysine having a molecular weight in a range of 1000 to 20,000, with succinic anhydride or glutaric anhydride, and which has a residual amino group ratio in a range of 70 to 93%, a mixture of the first and the second reactant have a molar ratio of an aldehyde group to an amino group in a range of 0.9 to 2.0, and the aldehyde-groups-introduced alpha-glucan is produced by oxidation of dextran or dextrin, with periodic acid or periodate, as to have aldehyde groups at a density of 0.1 to 1.0 per anhydroglucose unit.

12. The spray-coating system according to claim 11, wherein the adhesive powder is spray-coated on a wounded area by an amount of 20 to 50 mg/cm2 at one time of spray-coating operation.

13. The spray-coating system according to claim 12, wherein the molar ratio of the aldehyde group to the amino group is varied in a range of 0.2 to 0.4 so as to control a period of retaining a hydrated gel until breaking down in a range from two or three days to 4 weeks, the hydrated gel being formed by the adhesive powder in contact with aqueous liquid or moisture.

14. The spray-coating system according to claim 12, wherein the powder of aldehyde-groups-introduced alpha-glucan and the powder of partially carboxylated poly-L-lysine are porous.

15. The spray-coating system according to claim 9, wherein after the vibration motor starts the vibration motion, the valve is opened.

* * * * *